(12) United States Patent
Jagtap et al.

(10) Patent No.: US 7,268,143 B2
(45) Date of Patent: *Sep. 11, 2007

(54) ISOQUINOLINE DERIVATIVES AND METHODS OF USE THEREOF

(75) Inventors: Prakash Jagtap, Beverly, MA (US); Csaba Szabo, Gloucester, MA (US); Andrew L. Salzman, Belmont, MA (US); Aloka Roy, Acton, MA (US); William Williams, Ipswich, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/963,293

(22) Filed: Oct. 12, 2004

(65) Prior Publication Data

US 2005/0049270 A1 Mar. 3, 2005

Related U.S. Application Data

(60) Division of application No. 10/376,746, filed on Feb. 28, 2003, now Pat. No. 6,956,035, which is a continuation-in-part of application No. 10/233,198, filed on Aug. 30, 2002, now Pat. No. 6,828,319, which is a continuation-in-part of application No. 09/944,524, filed on Aug. 31, 2001, now abandoned.

(51) Int. Cl.
*A61K 31/4745* (2006.01)
*A61K 31/5377* (2006.01)
*C07D 471/06* (2006.01)
*C07D 413/14* (2006.01)

(52) U.S. Cl. .................. 514/285; 546/70; 544/125; 514/232.8; 514/232.5

(58) Field of Classification Search ................ 514/285, 514/232.8; 546/70; 544/125
See application file for complete search history.

(56) References Cited

U.S. PATENT DOCUMENTS

| | | | |
|---|---|---|---|
| 3,710,795 A | 1/1973 | Higuchi et al. | |
| 4,113,731 A | 9/1978 | Winters et al. | |
| 4,263,304 A | 4/1981 | Ishizumi et al. | |
| 5,079,246 A | 1/1992 | Forbes et al. | |
| 5,260,316 A | 11/1993 | Van Duzer et al. | |
| 5,262,564 A | 11/1993 | Kun et al. | |
| 5,597,831 A | 1/1997 | Michalsky et al. | |
| 5,710,162 A | 1/1998 | Okazaki et al. | |
| 5,733,918 A | 3/1998 | Okazaki et al. | |
| 6,028,079 A | 2/2000 | Okazaki et al. | |
| 6,346,535 B1 | 2/2002 | Cotter et al. | |
| 6,346,536 B1 | 2/2002 | Li et al. | |
| 6,498,194 B2 | 12/2002 | Cotter et al. | |
| 6,635,642 B1 | 10/2003 | Jackson et al. | |
| 6,828,319 B2 * | 12/2004 | Jagtap et al. ............ | 514/232.8 |
| 6,956,035 B2 | 10/2005 | Jagtap et al. | |
| 2002/0099063 A1 | 7/2002 | Cotter et al. | |
| 2003/0096833 A1 | 5/2003 | Jagtap et al. | |
| 2004/0039009 A1 | 2/2004 | Jagtap et al. | |

FOREIGN PATENT DOCUMENTS

| | | |
|---|---|---|
| CA | 2349227 | 5/2000 |
| GB | 2025932 B2 | 1/1980 |
| JP | 2003267888 | 9/2003 |
| WO | WO93/05023 | 3/1993 |
| WO | WO99/08680 | 2/1999 |
| WO | WO99/11311 | 3/1999 |
| WO | WO99/11623 | 3/1999 |
| WO | WO99/11628 | 3/1999 |
| WO | WO99/11644 | 3/1999 |
| WO | WO99/11645 | 3/1999 |
| WO | WO99/11649 | 3/1999 |
| WO | WO99/59973 | 11/1999 |
| WO | WO99/59975 | 11/1999 |
| WO | WO 00/21537 | 4/2000 |
| WO | WO 00/39070 | 7/2000 |
| WO | WO 00/39104 | 7/2000 |
| WO | WO 00/42040 | 7/2000 |
| WO | WO 01/12199 | 2/2001 |
| WO | 01/90077 A1 | 11/2001 |
| WO | WO 02/26284 | 1/2002 |
| WO | WO-04/014862 A1 | 2/2004 |
| WO | 2005/012524 A1 | 2/2005 |
| WO | 2005/053662 A1 | 6/2005 |

OTHER PUBLICATIONS

Aldrich, p. 32, Aldrich Chemical Company, 1992.
Bloch et al., The role of the 5'-hydroxyl group of adenosine in determining substrate specificity for adenosine deaminase, J. Med. Chem., 10(5):908-912, 1967.
Burger's Medicinal Chemistry and Drug Discovery, 5th ed., vol. 1:Principles and Practice, John Wiley and Sons, Inc., pp. 975-977, 1994.
Hakimelahi et al., Ring Open Analogues of Adenine Nucleoside, Aminoacyl Derivatives of Cyclo-and Acyclo-nucleosides, Helvetica Chemica Acta, 70:219-231, 1987.
Hiremath et al., A New Method for the Synthesis of 6H, 11H-Indolo[3,2-c]-isoquinolin-5-ones/thiones and their Reactions, J. Heterocyc. Chem., 30(3):603-609, 1993.
Kawana et al., Nucleoside Peptides. III. The Synthesis of N-[1-(9-Adenyl)-β-D-ribofuranuronosyl] Derivatives of Certain Amino Acids and Peptides, J. Org. Chem., 37(2):288-290, 1972.
Mandir et al., A novel in vivo post-translational modification of p53 by PARP-1 in MPTP-induced parkinsonism, J. Neurochem., 83(1):186-192, 2002.

(Continued)

*Primary Examiner*—Charanjit S. Aulakh
(74) *Attorney, Agent, or Firm*—Wilmer Cutler Pickering Hale and Dorr LLP

(57) ABSTRACT

The invention provides novel classes of Isoquinoline Derivatives. Pharmaceutical compositions and methods of making and using the compounds, are also described.

5 Claims, No Drawings

OTHER PUBLICATIONS

Mandir et al., Poly(ADP-ribose) polymerase activation mediates 1-methyl-4-phenyl-1, 2,3,6-tetrahydropyridine (MPTP)-induced parkinsonism, Proc. Natl. Acad. Sci. U.S.A., 96(10):5774-5779, 1999.

Ojika et al, Ptaquiloside, a Potent Carcinogen Isolated From Bracken Fem Pteridium Aquilinum Var. Latiusculum: Structure Elucidation Based On Chemical and Spectral Evidence, and Reactions with Amino Acids, Nucleosides, and Nucleotides, Tetrahedron, 43(22):5261-5274, 1987.

Wang et al., Apoptosis inducing factor and PARP-mediated injury in the MPTP mouse model of Parkinson's disease, Ann N.Y. Acad. Sci., 991:132-139, 2003.

Yamaguchi et al., The Synthesis of Benzofuroquinolines. IX. A Benzofuroisoquinolinone and a Benzofuroisocoumarin, J. Hetercycl. Chem., 32(2):419-423, 1995.

Abdelkarim et al., Protective effects of PJ34, a novel, potent inibitor of poly(ADP-ribose) polymerase (PARP) in in vitro and in vivo models of stroke, Int. J. Mol. Med., 7:255-260, 2001.

Ando et al., Cyclization reactions of 1,2-bis(2-cyanophenyl_propionitriles. II. Synthesis of 5-amino-4,7-dimethoxy-11H-indo[1,2-c]isoquinolin-11-one, Bull. Chem. Soc. Japan, 47:1014-17, 1974.

Banasik et al., Specific inhibitors of poly(ADP-ribose) synthetase and mono(ADP-ribosyl)transferase, J. Biol. Chem., 267:1569-75, 1992.

Banasik et al., Inhibitors and activators of ADP-ribosylation reactions, Mol. Cell. Biochem., 138:185-97, 1994.

Chatterjea et al., Cyclisation of alpha-benzylhomophthalic acids, Experientia, 16:439-440, 1960.

Chatterjea et al., On 4-Keto-3:4-Dihydrolsocoumarin, J. Indian Chem. Soc. 44(11):911-919, 1967.

Cushman et al., Synthesis of new indeno[1,2b]isoquinolines: Cytotoxic non-camptothecin topoisomerase I inhibitors, J. Med. Chem., 43(20):3688-3698, 2000.

Dusemund et al., 5-hydroxyisoindolo[2,1b]isoquinotin-7-one: Synthesis and isomerization, Arch. Pharm (Weinheim, Ger.), 317:381-2, 1984.

Griffin et al., Resistance-modifying agents. 5. Synthesis and biological properties of quinazolinone inhibitors of the DNA repair enzyme poly(ADP-ribose) polymerase (PARP), J. Med. Chem., 41:5247-5256, 1998.

Grupp et al., Protection against hypoxia-reoxygenation in the absence of poly9ADP-ribose) synthetase in isolated working hearts, J. Mol. Cell Cardiol., 31:297-303, 1999.

Hiremath et al., Synthesis of Substituted 7H-Indolo[2,3-c] isoquinolines, Indian Journal of Chemistry, Section B 24B(12):1235-1238, 1985.

Hiremath et al., Synthesis and Biological Evaluation of Some Substituted 5H, 6H, 7H,-Indolo[2,3-C] Isoquinolin-5-thiones and their Derivatives, Indian Journal of Heterocyclic Chemistry 3(1):37-42, 1993.

Hiremath et al., Synthesis of [10-substituted-6H,7H-indolo[2,3-c]iso-quinolin-5-one-6-yl]acetyl-3,5-disubstituted-pyrazoles/ pryazolones and 5-[10-substituted-6H,7H-indolo[2,3-c]iso-quinolin-5-one-6-yl]methyl-1,3,4-oxadiazol-2-thiones, Journal of the Indian Chemical Society 72(10):735-738, 1995.

Hiremath et al., Synthesis and Biological Studies of Some New Brideghead Nitrogen Heterocycles Containing Indoloisoquinoline Nucleus, Oriental Journal of Chemistry 13(2):173-176, 1997.

Hiremath et al., Synthesis of substituted 2-(5-oxo/thioxo-1,3,4-oxadiazol-2-yl)-indoles & 2-(5-oxo/thioxo-1,3,4-oxadiazol-2-ylamino)indoles, Indian Journal of Chemistry, Section B 22B(6):571-576, 1983.

Jantzen and Robinson, Modern Pharmaceutics, 3rd ed., eds. Baker and Rhodes, p. 596, 1995.

Jha et al., Synthesis of Indeno[2,1-c] isocoumarins and indeno[2,1-c]isoquinolones, Indian Journal of Chemistry, Section B 24B(4):440-444, 1985.

Kirby et al., Hydride hyperconjugation in 1(3)-methylazulenes, Tetrahedron Lett., 27:1-4, 1960.

Kirby et al., 4,6,8-trimethylazulenium percholrate, Chemistry & Industry (London, UK), 1217-1218, 1960.

Lal et al., Applications of carbon-nitrogen bond cleavage reaction: A synthesis/derivisation of 11H-indeno[1,2-c]isoquinolones, Indian J. Chem., Sect. B, 38B:33-39, 1999.

Lamping et al., LPS_binding protein protects mice from septic shock caused by LPS or gram-negative bacteria, J. Clin. Invest., 101(10):2065-2071, 1998.

Mabley et al., Inhibition of poly(ADP-ribose) synthetase by gene disruption or inhibitin with 5-iodo-6-amino-1,2-benzopyrone protects mice from multiple-low-dose-streptozotocin-induced diabetes, Br. J. Pharmacol., 133(6):909-919, 2001.

Milam et al., Inhibitors of poly(adenosine diphosphate-ribose) synthesis: effect on other metabolic processes. Science, 223:589-591, 1984.

Morrison and Boyd, Organic Chemistry, 5th ed., Allyn and Bacon, Inc., p. 179, 1987.

Ohno et al., Modulation of adenosine receptor affinity and intrinsic efficacy in adenine nucleosides substituted at the 2 position, Biorg. Med. Chem., 12:2995-3007, 2004.

Parrillo, Pathogenic mechanisms of septic shock, N. Eng. J. Med., 328:1471-1477, 1993.

Shinkwin et al., Synthesis of thiophenecarboxamides, thieno[3,4-c]pyridin-4(5H)-ones and thieno[3,4-d]pyrimidin-4(3H)-ones and preliminary evaluation as inhibitors of poly(ADP-ribose)polymerase (PARP). Bioorg. Med. Chem., 7:297-308, 1999.

Soriano et al., Diabetic endothelial dysfunction: the role of poly(ADP-ribose) polymerase activation. Nature Medicine, 7(1):108-113, 2001.

Southan and Szabo, Poly(ADP-ribose) polymerase inhibitors, Curr. Med. Chem., 10:321, 2003.

Srivastava et al., Synthesis of Indeno[2,1-c] isocoumarins and indeno [2,1-c]isoquinolones, Journal of the Indian Chemical Society 66(4):276-81, 1989.

Strumberg et al., Synthesis of cytotoxic indenosoquinoline topoisomerase I poisons, J. Med. Chem., 42(3):446-457, 1999.

Szabo et al., The pathophysiological role of peroxynitrite in shock, inflammation, and ischemia-reperfusion injury. Shock 6:79-88, 1996.

Szabo et al., Role of poly(ADP-ribose) synthetase in inflammation and ischaemia-reperfusion. Trends Pharmacol. Sci. 19:287-98, 1998.

Virag et al., Peroxynitrite-induced thymocyte apoptosis: the role of caspases and poly(ADP-ribose) synthetase (PARP) activation, Immunol., 94(3):345-355, 1998.

Wawzonek et al., Synthesis of 6-substituted-6H-indeno[1,2-c]isoquinoline-5,11-diones, Org. Prep. Proc. Int., 14:163-8, 1982.

Wawzonek et al., Preparation and reactions of 4b-acetoxy-4b,9b-dihydroindeno[2,1-a]indene-5, 10-dione, Can. J. Chem., 59:2833, 1981.

White et al., Resistance-modifying agents. 9. Synthesis and biological properties of benzimidazole inhibitors of the DNA repair enzyme poly(ADP-ribose) polymerase, J. Med. Chem., 43:4084-4097, 2000.

Winters et al., Synthesis and biological activities of some indolo[2,3-c]isoquinoline derivatives. Farmaco. Ed. Sci. 34(6):507-517, 1979.

Yamaguchi et al., The synthesis of benzofuroquinolines. X. Some benzofuro[3,2-c]isoquinoline derivatives, J. Hetercycl. Chem., 32(5):1517-1520, 1995.

Zhang et al., GPI 6150 prevents H(2)O(2) cytotoxicity by inhibiting poly(ADP-ribose) polymerase. Biochem. Biophys. Res. Commun., 278:590-98, 2000.

Mandir et al., Poly(ADP-ribose) Activation Mediates 1-methyl-4-phenyl-1,2,3,6-tetrahydropyridine (MPTP)-Induced Parkinsonism, *Proc. Nat. Acad. Sci.* USA 96 :5774-5779 (1999).

Jijon et al., Inhibition of poly(ADP-ribose) Polymerase Attenuates Inflammation in a Model of Chronic Colitis, *Am. J. Physiol. Gastrointest. Liver Physiol.* 279:G641-G651 (2000).

Szabo et al., Role of poly(ADP-ribose) Synthetase in Inflammation and Ischaemia-reperfusion, *Trends in Pharm. Sci.* 19:287-298 (1998).

Virag et al., The Therapeutic Potential of Poly(ADP-Ribose) Polymerase Inhibitors, *Pharmacol. Rev.* 54:375-429 (2002).

Lohinai et al., Role of the Activation of the Nuclear Enzyme Poly(ADP-Ribose) Polymerase in the Pathogenesis of Periodontitis, *J. Dent. Res.* 82:987-992 (2003).

Virag et al., Effects of poly(ADP-Ribose) Polymerase Inhibition on Inflammatory Cell Migration in a Murine Model of Asthma, *Med. Sci. Monit.* 10:BR77-BR83 (2004).

Szabo et al., Roles of poly(ADP-ribose) Polymerase Activation in the Pathogenesis of Diabetes mellitus and its Complications, *Pharmacol. Res.* 52:60-71 (2005).

Szabo et al., Poly(ADP-Ribose) Polymerase Inhibition Reduces Reperfusion Injury After Heart Transplantation, *Circulation Research* 90:100-106 (2002).

Pacher et al., Role of Nitrosative Stress and Peroxynitrite in the Pathogenesis of Diabetic Complications. Emerging New Therapeutical Strategies, *Curr. Med. Chem.* 12:267-275 (2005).

Wawzonek et al., The Synthesis and Reactions of 1-Carbamyl-11-ketoindeno[1,2-c]isoquinoline, *J. Org. Chem.* 31:1004-1006 (1966).

Jagtap et al., Facile and Convenient Synthesis of 6,11-Dihydro-5*H*-indeno[1,2-*c*]isoquinolin-5-ones and 6,11-Dihydro-5*H*-indolo[3,2-*c*]isoquinolin-5-one, *Org. Lett.* 7:1753-1756 (2005).

Chatterjea, J.N. et al, The Course of Cyclisation of α-Benzylhomophthalic Acids. Part 1. A New Route to 2:3-6:7 Dibenzotropones, Jour. Indian Chem. Soc., vol. 37, No. 7, 1960.

\* cited by examiner

ISOQUINOLINE DERIVATIVES AND METHODS OF USE THEREOF

This application is a division of U.S. application Ser. No. 10/376,746, filed Feb. 28, 2003 now U.S. Pat. No. 6,956,035, which is (a) a continuation-in-part of U.S. application Ser. No. 10/233,198, filed Aug. 30, 2002 now U.S. Pat. No. 6,828,319, which is a continuation-in-part of U.S. application Ser. No. 09/944,524, filed Aug. 31, 2001 now abandoned, the entire disclosure of each of the aforementioned applications being incorporated by reference herein in its entirety.

This invention was made with government support under grant no. R44 DK54099-03 and grant no. 1R43 CA90016-01A1, which were awarded by the National Institutes of Health. The government has certain rights in the invention.

1. FIELD OF THE INVENTION

The invention relates to Isoquinoline Derivatives; compositions comprising an Isoquinoline Derivative; and methods for treating or preventing an inflammatory disease or a reperfusion disease comprising the administration of an effective amount of an Isoquinoline Derivative.

2. BACKGROUND OF THE INVENTION

Inflammatory diseases, such as arthritis, colitis, and autoimmune diabetes, typically manifest themselves as disorders distinct from those associated with reperfusion diseases, e.g., stroke and heart attack, and can clinically manifest themselves as different entities. However, there can be common underlying mechanisms between these two types of disorders. In particular, inflammatory disease and reperfusion disease can induce proinflammatory cytokine and chemokine synthesis which can, in turn, result in production of cytotoxic free radicals such as nitric oxide and superoxide. NO and superoxide can react to form peroxynitrite ($ONOO^-$) (Szabó et al., Shock 6:79–88, 1996).

The $ONOO^-$-induced cell necrosis observed in inflammatory disease and in reperfusion disease involves the activation of the nuclear enzyme poly (ADP-ribose) synthetase (PARS). Activation of PARS is thought to be an important step in the cell-mediated death observed in inflammation and reperfusion disease (Szabó et al., Trends Pharmacol. Sci. 19: 287–98, 1998).

A number of PARS inhibitors have been described in the art. See, e.g., Banasik et al., J. Biol. Chem., 267:1569–75, 1992, and Banasik et al., Mol. Cell. Biochem., 138:185–97, 1994; WO 00/39104; WO 00/39070; WO 99/59975; WO 99/59973; WO 99/11649; WO 99/11645; WO 99/11644; WO 99/11628; WO 99/11623; WO 99/11311; WO 00/42040; Zhang et al., Biochem. Biophys. Res. Commun., 278:590–98, 2000; White et al., J. Med. Chem., 43:4084–4097,2000; Griffin et al., J. Med. Chem., 41:5247–5256, 1998; Shinkwin et al., Bioorg. Med. Chem., 7:297–308, 1999; and Soriano et al., Nature Medicine, 7:108–113, 2001. Adverse effects associated with administration of PARS inhibitors have been discussed in Milan et al, Science, 223:589–591, 1984.

Isoquinoline compounds have been previously discussed in the art. For example, cytotoxic non-camptothecin topoisomerase I inhibitors are reported in Cushman et al., J. Med. Chem., 43:3688–3698, 2300 and Cushman et al., J. Med. Chem. 42:446–57, 1999; indeno[1,2-c]isoquinolines are reported as antineoplastic agents in Cushman et al., WO 00/21537; and as neoplasm inhibitors in Hrbata et al., WO 93/05023.

Syntheses of isoquinoline compounds have been reported. For example, see Wawzonek et al., Org. Prep. Proc. Int. 14:163–8, 1982; Wawzonek et al., Can. J. Chem. 59:2833, 1981; Andoi et al., Bull. Chem. Soc. Japan, 47:1014–17, 1974; Dusemund et al., Arch. Pharm (Weinheim, Ger.), 3 17:381–2, 1984; and Lal et al., Indian J. Chem., Sect. B, 38B:33–39, 1999.

There remains, however, a need in the art for compounds useful for treating or preventing inflammatory diseases or reperfusion diseases.

Citation of any reference in Section 2 of this application is not an admission that the reference is prior art.

3. SUMMARY OF THE INVENTION

The invention is based in part on the discovery of novel substituted tetracyclic benzamide derivatives and their demonstrated effects in the treatment of inflammation, cell death and in treating shock and reperfusion diseases.

Accordingly, in one aspect the invention includes a compound of Formula I, Formula Ia, Formula Ib, Formula II, Formula III, Formula 13, Formula 22, Formula 37 or Formula 40, or a pharmaceutically acceptable salt or hydrate thereof (an "Isoquinoline Derivative") as set forth below in the Detailed Description of the Invention.

Also provided by the invention is a method for treating or preventing an inflammatory disease or a reperfusion disease in a subject, comprising administering to a subject in need of such treatment or prevention an effective amount of an Isoquinoline Derivative.

In a further aspect, the invention also includes methods for making an Isoquinoline Derivative of Formula Ia, Formula Ib, Formula II, Formula III, Formula 13, Formula 22, Formula 37 or Formula 40.

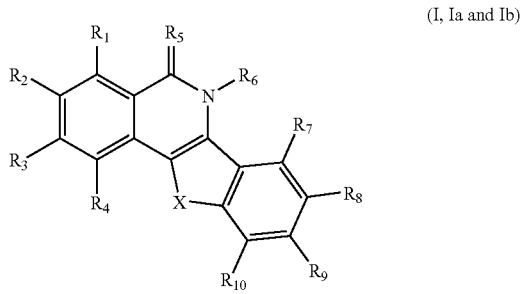

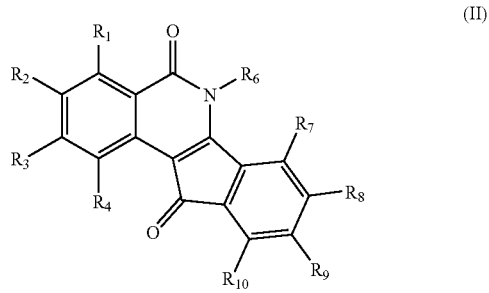

-continued (III)

(13)

(22)

(37)

(40)

The Isoquinoline Derivatives can be used to treat or prevent a variety of conditions and diseases, including, but not limited to, an inflammatory disease or a reperfusion disease.

The invention also includes pharmaceutical compositions that comprise an effective amount of an Isoquinoline Derivative and a pharmaceutically acceptable carrier. The compositions are useful for treating or preventing an inflammatory disease or a reperfusion disease. The invention includes an Isoquinoline Derivative when provided as a pharmaceutically acceptable prodrug, a hydrated salt, such as a pharmaceutically acceptable salt, or mixtures thereof.

The details of the invention are set forth in the accompanying description below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

4. DETAILED DESCRIPTION OF THE INVENTION

The present invention provides Isoquinoline Derivatives according to Formula I, Formula Ia, Formula Ib, Formula II, Formula III, Formula 13, Formula 37 and Formula 40 as set forth below:

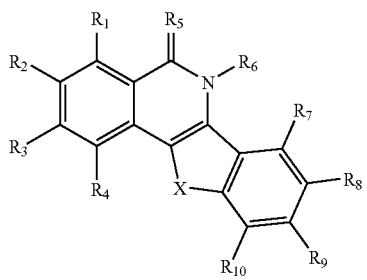

(I)

and pharmaceutically acceptable salts and hydrates thereof, wherein:

$R_5$ is NH or S;

$R_6$ is —H or $C_1$–$C_4$ alkyl;

X is —C(O)—, —CH$_2$—, —CH(halo)—, —CH(OH)—(CH$_2$)$_n$—, —CH(OH)-arylene—, —O—, —NH—, —S—, —CH(NR$_{11}$R$_{12}$)— or —N(SO$_2$Y)—, wherein Y is —OH, —NH$_2$ or -alkylheterocycle and n is an integer ranging from 0–5;

$R_{11}$ and $R_{12}$ are independently -hydrogen or —$C_1$–$C_9$ alkyl, or N, $R_{11}$ and $R_{12}$ are taken together to form a heterocyclic amine;

$R_1$ is -hydrogen, -halo, —$C_1$–$C_{10}$ alkyl, -alkylhalo, —$C_2$–$C_{10}$ alkenyl, —$C_3$–$C_8$ carbocycle, -aryl, —NH$_2$, -alkylamino, —C(O)OH, —C(O)O($C_1$–$C_5$ alkyl), NO$_2$ or —A—B;

A is —SO$_2$—, —SO$_2$NH—, —NHCO—, —NH-CONH—, —CO—, —C(O)O—, —CONH—, —CON($C_1$–$C_4$ alkyl)—, —NH—, —CH$_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —NZ$_1$Z$_2$, —($C_1$–$C_5$ alkylene)-NZ$_1$Z$_2$, -alkylamino, -aminodialkyl, -alkylheterocycle, -arylamido, —C(O)OH, —C(O)O—($C_1$–$C_5$ alkyl), —C(O)O-phenyl or —C(NH)NH$_2$ any of which are unsubstituted or substituted with one or more of —O—($C_1$–$C_5$ alkyl), -halo, -alkylhalo, -alkanol, -alkylamino, -hydroxy, —NO$_2$, —NH$_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —C(O)OH, —$C_1$–$C_5$ alkylene-C(O)O—($C_1$–$C_5$ alkyl) or —$C_1$–$C_5$ alkylene-OC(O)—($C_1$–$C_5$ alkyl);

$R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or —A—B; and at least one of $R_1$, $R_2$, $R_3$, $R_4$, $R_7$, $R_8$, $R_9$ or $R_{10}$ is other than hydrogen;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NZ_1Z_2$, —($C_1$–$C_5$ alkylene)-$NZ_1Z_2$, -alkylamino, -aminodialkyl, -alkylheterocycle, -arylamido, —C(O)OH, —C(O)O—($C_1$–$C_5$ alkyl), —C(O)O-phenyl or —C(NH)$NH_2$ any of which are unsubstituted or substituted with one or more of —O—($C_1$–$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —C(O)OH, —$C_1$–$C_5$ alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, X is —C(O)—, —$CH_2$—, —CH(halo)-, —CH(OH)—($CH_2$)$_n$—, —CH(OH)—arylene-, —O—, —NH—, —S— or —CH($NR_{11}R_{12}$)—, wherein n is an integer ranging from 0–5.

In another embodiment B is —$C_1$–$C_{10}$ alkyl, —$C_2$–$C_{10}$ alkenyl, -heterocycle, —$C_3$–$C_8$ carbocycle, -aryl, —$NZ_1Z_2$, -alkylamino, -aminodialkyl, -alkylheterocycle, -arylamido, —C(O)OH, —C(O)O—($C_1$–$C_5$ alkyl) or —C(O)O-phenyl, any of which are unsubstituted or substituted with one or more of —O—($C_1$–$C_5$ alkyl), -halo, -alkylhalo, -alkanol, -alkylamino, -hydroxy, —$NO_2$, —$NH_2$, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —$C_1$–$C_5$ alkylene-C(O)O—$C_1$–$C_5$ alkyl or —$C_1$–$C_5$ alkylene-OC(O)—$C_1$–$C_5$ alkyl.

In another embodiment, $R_1$–$R_4$ are hydrogen.

In a further embodiment at least one of $R_1$, $R_2$, $R_3$, $R_4$, $R_7$, $R_8$, $R_9$ and $R_{10}$ is other than hydrogen.

The invention also relates to a compounds of formula (Ia):

(Ia)

and pharmaceutically acceptable salts and hydrates thereof, wherein:

$R_5$ is NH or S;
$R_6$ is —H or $C_1$–$C_4$ alkyl;

X is —C(O)—, —$CH_2$—, —CH(halo)-, —CH(OH)—($CH_2$)$_n$—, —CH(OH)-arylene-, —O—, —NH—, —S—, —CH($NR_{11}R_{12}$)— or —N($SO_2Y$)—, wherein Y is —OH, —$NH_2$ or -alkylheterocycle and n is an integer ranging from 0–5;

$R_{11}$ and $R_{12}$ are independently -hydrogen or —$C_1$–$C_9$ alkyl, or N, $R_{11}$ and $R_{12}$ are taken together to form a heterocyclic amine;

$R_1$ is -hydrogen, -halo, —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), $NO_2$ or —A'—B';

A' is —$SO_2$—, —$SO_2NH$—, —NHCO—, —NHCONH—, —CO—, —C(O)O—, —CONH—, —CON($C_1$–$C_4$ alkyl)-, —NH—, —$CH_2$—, —S— or —C(S)—;

B' is —$C_1$–$C_{10}$ alkyl, —$C_2$–$C_{10}$ alkenyl, -heterocycle, —$C_3$–$C_8$ carbocycle, -aryl, —$NZ_1Z_2$, —($C_1$–$C_5$ alkylene)-$NZ_1Z_2$, -alkylamino, -aminodialkyl, -alkylheterocycle, -arylamido, —C(O)OH, —C(O)O—($C_1$–$C_5$ alkyl), —C(O)O-phenyl or —C(NH)$NH_2$ any of which are unsubstituted or substituted with one or more of —O—($C_1$–$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —C(O)OH, —$C_1$–$C_5$ alkylene-C(O)O—($C_1$–$C_5$ alkyl) or —$C_1$–$C_5$ alkylene-OC(O)—($C_1$–$C_5$ alkyl);

$R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or —A—B; and at least one of $R_1$, $R_2$, $R_3$, $R_4$, $R_7$, $R_8$, $R_9$ or $R_{10}$ is other than hydrogen;

A is —$SO_2$—, —$SO_2NH$—, —NHCO—, —NHCONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NZ_1Z_2$, —($C_1$–$C_5$ alkylene)-$NZ_1Z_2$, -alkylamino, -aminodialkyl, -alkylheterocycle, -arylamido, —C(O)OH, —C(O)O—($C_1$–$C_5$ alkyl), —C(O)O-phenyl or —C(NH)$NH_2$ any of which are unsubstituted or substituted with one or more of —O—($C_1$–$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —C(O)OH, —$C_1$–$C_5$ alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, X is —C(O)—, —$CH_2$—, —CH(halo)-, —CH(OH)—($CH_2$)$_n$—, —CH(OH)—arylene-, —O—, —NH—, —S— or —CH($NR_{11}R_{12}$)—, wherein n is an integer ranging from 0–5.

In another embodiment B is —$C_1$–$C_{10}$ alkyl, —$C_2$–$C_{10}$ alkenyl, -heterocycle, —$C_3$–$C_8$ carbocycle, -aryl, —$NZ_1Z_2$, -alkylamino, -aminodialkyl, -alkylheterocycle, -arylamido, —C(O)OH, —C(O)O—($C_1$–$C_5$ alkyl) or —C(O)O-phenyl, any of which are unsubstituted or substituted with one or more of —O—($C_1$–$C_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C$_1$–C$_5$ alkylene-C(O)O—C$_1$–C$_5$ alkyl or —C$_1$–C$_5$ alkylene-OC(O)—C$_1$–C$_5$ alkyl.

In another embodiment, R$_1$–R$_4$ are hydrogen.

In a further embodiment at least one of R$_1$, R$_2$, R$_3$, R$_4$, R$_7$, R$_8$, R$_9$ and R$_{10}$ is other than hydrogen.

In one embodiment, A is —SO$_2$—.

In other illustrative embodiments R$^5$ and X in a compound of formula Ia are as set forth below:

| R$^5$ | X |
|---|---|
| NH | —C(O)— |
| NH | —CH$_2$— |
| NH | —CH(halo)— |
| NH | —CH(OH)(CH$_2$)$_n$— |
| NH | —CH(arylene)(OH)— |
| NH | —O— |
| NH | —NH— |
| NH | —S— |
| NH | —CH(NR$^{11}$R$^{12}$)— |
| NH | —N(SO$_2$Y)— |
| S | —C(O)— |
| S | —CH$_2$— |
| S | —CH(halo)— |
| S | —CH(OH)(CH$_2$)$_n$— |
| S | —CH(arylene)(OH)— |
| S | —O— |
| S | —NH— |
| S | —S— |
| S | —CH(NR$^{11}$R$^{12}$)— |
| S | —N(SO$_2$Y)— |

The invention also relates to compounds of Formula Ib:

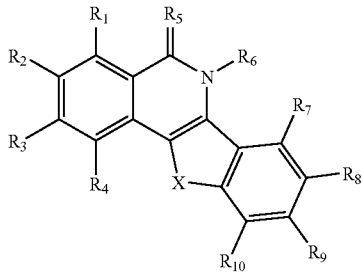

(Ib)

and pharmaceutically acceptable salts and hydrates thereof, wherein:

R$_5$ is NH or S;

R$_6$ is —H or C$_1$–C$_4$ alkyl;

X is —C(O)—, —CH$_2$—, —CH(halo)-, —CH(OH)—(CH$_2$)$_n$—, —CH(OH)-arylene-, —O—, —NH—, —S—, —CH(NR$_{11}$R$_{12}$)— or —N(SO$_2$Y)—, wherein Y is —OH, —NH$_2$ or -alkylheterocycle and n is an integer ranging from 0–5;

R$_{11}$ and R$_{12}$ are independently -hydrogen or —C$_1$–C$_9$ alkyl, or N, R$_{11}$ and R$_{12}$ are taken together to form a heterocyclic amine;

R$_1$ is -hydrogen, -halo, —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), NO$_2$ or —A'—B';

A' is —SO$_2$—, —SO$_2$NH—, —NHCO—, —NH-CONH—, —CO—, —C(O)O—, —CONH—, —CON(C$_1$–C$_4$ alkyl)—, —NH—, —CH$_2$—, —S— or —C(S)—;

B' is —C$_1$–C$_{10}$ alkyl, —C$_2$–C$_{10}$ alkenyl, -heterocycle, —C$_3$–C$_8$ carbocycle, -aryl, —NZ$_1$Z$_2$, —(C$_1$–C$_5$ alkylene)-NZ$_1$Z$_2$, -alkylamino, -aminodialkyl, -alkylheterocycle, -arylamido, —C(O)OH, —C(O)O—(C$_1$–C$_5$ alkyl), —C(O)O-phenyl or —C(NH)NH$_2$ any of which are unsubstituted or substituted with one or more of —O—(C$_1$–C$_5$ alkyl), -halo, -alkylhalo, -alkanol, -alkylamino, -hydroxy, —NO$_2$, —NH$_2$, —CN, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C(O)OH, —C$_1$–C$_5$ alkylene-C(O)O—(C$_1$–C$_5$ alkyl) or —C$_1$–C$_5$ alkylene-OC(O)—(C$_1$–C$_5$ alkyl);

R$_2$, R$_3$, R$_4$, R$_7$, R$_8$, R$_9$ and R$_{10}$ are independently -hydrogen, -halo, -hydroxy, —O—(C$_1$–C$_5$ alkyl), —C$_1$–C$_{10}$ alkyl, -alkylhalo, —C$_2$–C$_{10}$ alkenyl, —C$_3$–C$_8$ carbocycle, -aryl, —NH$_2$, -alkylamino, —C(O)OH, —C(O)O(C$_1$–C$_5$ alkyl), —OC(O)(C$_1$–C$_5$ alkyl), NO$_2$ or —A—B; and at least one of R$_1$, R$_2$, R$_3$, R$_4$, R$_7$, R$_8$, R$_9$ or R$_{10}$ is other than hydrogen;

A is —SO$_2$—, —SO$_2$NH—, —NHCO—, —NH-CONH—, —O—, —CO—, —OC(O)—, —C(O)O—, —CONH—, —CON(C$_1$–C$_4$ alkyl)-, —NH—, —CH$_2$—, —S— or —C(S)—;

B is —C$_1$–C$_{10}$ alkyl, —C$_2$–C$_{10}$ alkenyl, -heterocycle, —C$_3$–C$_8$ carbocycle, -aryl, —NZ$_1$Z$_2$, —(C$_1$–C$_5$ alkylene)-NZ$_1$Z$_2$, -alkylamino, -aminodialkyl, -alkylheterocycle, -arylamido, —C(O)OH, —C(O)O—(C$_1$–C$_5$ alkyl), —C(O)O-phenyl or —C(NH)NH$_2$ any of which are unsubstituted or substituted with one or more of —O—(C$_1$–C$_5$ alkyl), -halo, -alkylhalo, -alkanol, -alkylamino, -hydroxy, —NO$_2$, —NH$_2$, —CN, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C(O)OH, —C$_1$–C$_5$ alkylene-C(O)O—(C$_1$–C$_5$ alkyl) or —C$_1$–C$_5$ alkylene-OC(O)—(C$_1$–C$_5$ alkyl); and Z$_1$ and Z$_2$ are independently —H or —C$_1$–C$_{10}$ alkyl, which is unsubstituted or substituted with one or more of -halo, —OH or —N(Z$_3$)(Z$_4$), where Z$_3$ and Z$_4$ are independently, —H or —C$_1$–C$_5$ alkyl, which is unsubstituted or substituted with one or more of -halo, -hydroxy or —NH$_2$; or N, Z$_3$ and Z$_4$ are taken together to form an unsubstituted or substituted heterocyclic amine; or N, Z$_1$ and Z$_2$ are taken together to form a heterocyclic amine.

In one embodiment, X is —C(O)—, —CH$_2$—, —CH(halo)-, —CH(OH)—(CH$_2$)$_n$—, —CH(OH)—arylene-, —O—, —NH—, —S— or —CH(NR$_{11}$R$_{12}$)—, wherein n is an integer ranging from 0–5.

In another embodiment B is —C$_1$–C$_{10}$ alkyl, —C$_2$–C$_{10}$ alkenyl, -heterocycle, —C$_3$–C$_8$ carbocycle, -aryl, —NZ$_1$Z$_2$, -alkylamino, -aminodialkyl, -alkylheterocycle, -arylamido, —C(O)OH, —C(O)O—(C$_1$–C$_5$ alkyl) or —C(O)O-phenyl, any of which are unsubstituted or substituted with one or more of —O—(C$_1$–C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —C$_1$–C$_5$ alkylene-C(O)O—C$_1$–C$_5$ alkyl or —C$_1$–C$_5$ alkylene-OC(O)—C$_1$–C$_5$ alkyl.

In another embodiment, R$_1$–R$_4$ are hydrogen.

In a further embodiment at least one of R$_1$, R$_2$, R$_3$, R$_4$, R$_7$, R$_8$, R$_9$ and R$_{10}$ is other than hydrogen.

In one embodiment, A is —SO$_2$— or —SO$_2$NH$_2$—.

In yet another embodiment, R$_5$ is O.

In illustrative embodiments $R^5$ and X in a compound of formula Ib are as set forth below:

| $R^5$ | X |
|---|---|
| O | —$CH_2$— |
| O | —CH(halo)— |
| O | —CH(OH)$(CH_2)_n$— |
| O | —CH(arylene)(OH)— |
| O | —O— |
| O | —NH— |
| O | —S— |
| O | —CH($NR^{11}R^{12}$)— |
| O | —N($SO_2Y$)— |

Illustrative Compounds of Formula Ib are set forth below:

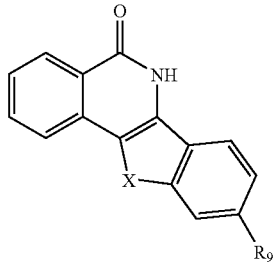

| Compound | $R_7$ | $R_8$ | $R_9$ | $R_{10}$ |
|---|---|---|---|---|
| 22a | —H | —H | —H | —H |
| 22b | —H | —OMe | —H | —H |
| 22c | —H | —H | —OMe | —H |
| 22d | —H | —H | —H | —OMe |
| 22e | —H | —Me | —H | —H |
| 22f | —H | —COOH | —H | —H |
| 22g | —H | —H | —COOH | —H |
| 23a | —H | —OH | —H | —H |
| 23b | —H | —H | —OH | —H |
| 23c | —H | —H | —H | —OH |
| 25a | —H | —H | —$(CH_2)_4OH$ | —H |
| 25b | —H | —H | —$(CH_2)_5OH$ | —H |
| 25c | —H | —H | —$(CH_2)_6OH$ | —H |
| 25d | —H | —H | —$(CH_2)_4COOH$ | —H |
| 25e | —H | —H | —$(CH_2)_5COOH$ | —H |
| 26a | —H | —C(O)NH$(CH_2)_3$-N-morpholine | —H | —H |
| 26b | —H | —C(O)NH$(CH_2)_2$—COOH | —H | —H |
| 26c | —H | —C(O)NH$(CH_2)_3$—N-(1,3-imidazole) | —H | —H |
| 26d | —H | —C(O)NH$(CH_2)_2$—$NMe_2$ | —H | —H | and pharmaceutically acceptable salts and hydrates thereof.

Additional Illustrative Compounds of Formula Ib are set forth below:

| Compound | X | $R_9$ |
|---|---|---|
| 31 | —NH— | —H |
| 34 | —N($SO_3H$)— | —$SO_3H$ |
| 35a | —N($SO_2NH_2$)— | —$SO_2NH_2$ |
| 35b | —N[$SO_2NH(CH_2)_3$(N-morpholine)]- | —$SO_2NH(CH_2)_3$(N-morpholine) |
| 40a | —S— | —H | and pharmaceutically acceptable salts and hydrates thereof.

The invention also relates to compounds of Formula II:

(II)

and pharmaceutically acceptable salts and hydrates thereof, wherein:

$R_6$ is —H or $C_1$–$C_4$ alkyl;

$R_1$ is -hydrogen, -halo, —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), $NO_2$ or —A'—B';

A' is —$SO_2$—, —$SO_2NH$—, —NHCO—, —NH-CONH—, —CO—, —C(O)O—, —CONH—, —CON($C_1$–$C_4$ alkyl)-, —NH—, —$CH_2$—, —S— or —C(S)—;

B' is —$C_1$–$C_{10}$ alkyl, —$C_2$–$C_{10}$ alkenyl, -heterocycle, —$C_3$–$C_8$ carbocycle, -aryl, —$NH_2$, -alkylamino, -aminodialkyl, -alkylheterocycle, -arylamido, —C(O)OH, —C(O)O—($C_1$–$C_5$ alkyl), —C(O)O-phenyl or —$NZ_1Z_2$;

$R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or —A—B; wherein at least one of $R^1$, $R^4$ and $R^{10}$ is other than hydrogen;

A is —$SO_2$—, —$SO_2NH$—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NH_2$, -alkylamino, -aminodialkyl, -alkylheterocycle, -arylamido, —C(O)OH, —C(O)O—($C_1$–$C_5$ alkyl), —C(O)O-phenyl or —$NZ_1Z_2$; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, B is a heterocyclic amine.

In another embodiment, B is arylalkyl.

In still another embodiment, $R_1$ is -hydrogen, -halo, —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), $NO_2$ or —A—B;

A is —$SO_2$—, —$SO_2NH$—, —NHCO—, —NH-CONH—, —CO—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NH_2$, -alkylamino, -aminodialkyl, -alkylheterocycle, -arylamido, —C(O)OH, —C(O)O—($C_1$–$C_5$ alkyl), —C(O)O-phenyl or —$NZ_1Z_2$.

In a further embodiment at least one of $R_1$, $R_2$, $R_3$, $R_4$, $R_7$, $R_8$, $R_9$ and $R_{10}$ is not hydrogen.

The invention also relates to compounds of Formula III:

(III)

and pharmaceutically acceptable salts and hydrates thereof, wherein:

X is —$CH_2$— or —O—;

$R_2$ and $R_3$ are independently -hydrogen, -halo, -alkylhalo, -hydroxy, —O—($C_1$–$C_5$ alkyl), —$C_1$–$C_3$ alkyl, —$NO_2$, —$NH_2$, —$CONH_2$, —C(O)OH, —OC(O)—$C_1$–$C_5$ alkyl or —C(O)O—$C_1$–$C_5$ alkyl;

$R_8$ and $R_9$ are independently -hydrogen or —A—B;

A is —$SO_2$—, —$SO_2NH$— or —NHCO—; and

B is —$C_1$–$C_3$ alkyl, —$NZ_1Z_2$, -heterocycle or -alkylamino, each unsubstituted or substituted with one or more of -alkanol, -alkylamino, -aminoalkyl, -aminodialkyl or -heterocycle, each unsubstituted or substituted with —$C_1$–$C_{10}$ alkyl or -alkanol; and $Z_1$ and $Z_2$ are independently -hydrogen or —$C_1$–$C_8$ alkyl, which is unsubstituted or substituted with one or more of -hydroxy or —$NZ_3Z_4$, where $Z_3$ and $Z_4$ are independently —H or —$C_1$–$C_3$ alkyl, which is unsubstituted or substituted with one or more of -hydroxy or —$NH_2$, or N, $Z_3$ and $Z_4$ are taken together to a heterocyclic amine, or N, $Z_1$ and $Z_2$ are taken together to form a heterocyclic amine.

In one embodiment, —X— is —$CH_2$—.

In another embodiment, —X— is —O—.

In one embodiment, $R^8$ is hydrogen and $R^9$ is —A—B.

In another embodiment, $R^8$ is —A—B and $R^9$ is hydrogen.

In one embodiment, either $R^8$ is hydrogen and $R^9$ is —A—B, or $R^8$ is —A—B and $R^9$ is hydrogen.

In one embodiment, $R^3$, $R^8$ and $R^9$ are hydrogen and $R^2$ is —A—B, wherein A is —NHC(O)—.

In another embodiment, $R^2$, $R^8$ and $R^9$ are hydrogen and $R^3$ is —A—B, wherein A is —NHC(O)—.

In still another embodiment $R^2$, $R^3$ and $R^8$ are hydrogen and $R^9$ is —A—B, wherein A is —$SO_2$— or —$SO_2NH$—.

In a further embodiment at least one of $R_2$, $R_3$, $R_8$ and $R_9$ is not hydrogen.

The invention further relates to compounds of Formula 13:

13 and pharmaceutically acceptable salts and hydrates thereof wherein $R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), $NO_2$ or —A—B;

A is —$SO_2$—, —$SO_2NH$—, —NHCO—, —NH-CONH—, —O—, —CO—, —OC(O)—, —C(O)O—, —CONH—, —CON($C_1$–$C_4$ alkyl)-, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NZ_1Z_2$, —($C_1$–$C_5$ alkylene)-$NZ_1Z_2$, -alkylamino, -aminodialkyl, -alkylheterocycle, -arylamido, —C(O)OH, —C(O)O—($C_1$–$C_5$ alkyl), —C(O)O-phenyl or —C(NH)$NH_2$ any of which are unsubstituted or substituted with one or more of —O—($C_1$–$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -alkylamido, -alkylcarboxy, —C(O)OH, —$C_1$–$C_5$ alkylene-C(O)O—($C_1$–$C_5$ alkyl) or —$C_1$–$C_5$ alkylene-OC(O)—($C_1$–$C_5$ alkyl); and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine.

In one embodiment, $R_9$ is —A—B, wherein —A— is —$SO_2$— or —$SO_2NH$—.

In another embodiment $R_1$–$R_4$ are each hydrogen.

In another embodiment, $R_1$–$R_4$ are each hydrogen.

In a further embodiment at least one of $R_1$, $R_2$, $R_3$, $R_4$, $R_7$, $R_8$, $R_9$ and $R_{10}$ is other than hydrogen.

The invention further still relates to compounds of Formula 22:

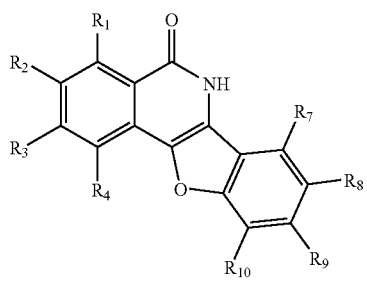

22 and pharmaceutically acceptable salts and hydrates thereof wherein $R_1$–$R_4$ and $R_7$–$R_{10}$ are as defined above for Formula 13.

In one embodiment, $R_9$ is —A—B, wherein —A— is —$SO_2$— or —$SO_2NH$—.

In another embodiment $R_1$–$R_4$ are each hydrogen.

In a further embodiment at least one of $R_1$, $R_2$, $R_3$, $R_4$, $R_7$, $R_8$, $R_9$ and $R_{10}$ is other than hydrogen.

The invention further still relates to compounds of Formula 37:

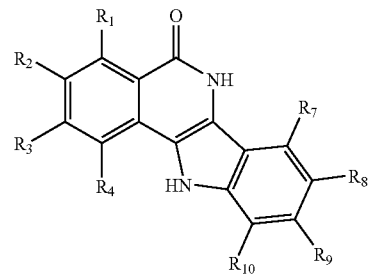

37 and pharmaceutically acceptable salts and hydrates thereof wherein $R_1$–$R_4$ and $R_7$–$R_{10}$ are as defined above for Formula 13.

In one embodiment $R_1$–$R_4$ are each hydrogen.

In a further embodiment at least one of $R_1$, $R_2$, $R_3$, $R_4$, $R_7$, $R_8$, $R_9$ and $R_{10}$ is other than hydrogen.

The invention also relates to compounds of Formula 40:

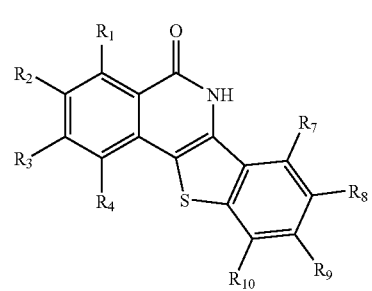

40 and pharmaceutically acceptable salts and hydrates thereof wherein $R_1$–$R_4$ and $R_7$–$R_{10}$ are as defined above for Formula 13.

In one embodiment $R_1$–$R_4$ are each hydrogen.

In a further embodiment at least one of $R_1$, $R_2$, $R_3$, $R_4$, $R_7$, $R_8$, $R_9$ and $R_{10}$ is other than hydrogen.

4.1 DEFINITIONS

The following definitions are used in connection with the Isoquinoline Derivatives:

"$C_1$–$C_3$ alkyl" refers to a straight or branched chain saturated hydrocarbon containing 1–3 carbon atoms. Examples of a $C_1$–$C_3$ alkyl group include, but are not limited to, methyl, ethyl, propyl and isopropyl "$C_1$–$C_4$ alkyl" refers to a straight or branched chain saturated hydrocarbon containing 1–4 carbon atoms. Examples of a $C_1$–$C_4$ alkyl group include, but are not limited to, methyl, ethyl, propyl, butyl, isopropyl, isobutyl, sec-butyl and tert-butyl.

"$C_1$–$C_5$ alkyl" refers to a straight or branched chain saturated hydrocarbon containing 1–4 carbon atoms. Examples of a $C_1$–$C_5$ alkyl group include, but are not limited to, methyl, ethyl, propyl, butyl, pentyl, isopropyl, isobutyl, sec-butyl and tert-butyl, isopentyl and neopentyl.

"$C_1$–$C_8$ alkyl" refers to a straight or branched chain saturated hydrocarbon containing 1–8 carbon atoms. Examples of a $C_1$–$C_8$ alkyl group include, but are not limited to, methyl, ethyl, propyl, butyl, pentyl, hexyl, heptyl, octyl, isopropyl, isobutyl, sec-butyl and tert-butyl, isopentyl, neopentyl, isohexyl, isoheptyl and isooctyl.

"$C_1$–$C_9$ alkyl" refers to a straight or branched chain saturated hydrocarbon containing 1–9 carbon atoms. Examples of a $C_1$–$C_9$ alkyl group include, but are not limited to, methyl, ethyl, propyl, butyl, pentyl, hexyl, heptyl, octyl, nonyl, isopropyl, isobutyl, sec-butyl and tert-butyl, isopentyl, neopentyl, isohexyl, isoheptyl, isooctyl and isononyl.

"$C_1$–$C_{10}$ alkyl" refers to a straight or branched chain saturated hydrocarbon containing 1–10 carbon atoms. Examples of a $C_1$–$C_{10}$ alkyl group include, but are not limited to, methyl, ethyl, propyl, butyl, pentyl, hexyl, heptyl, octyl, nonyl, decyl, isopropyl, isobutyl, sec-butyl and tert-butyl, isopentyl, neopentyl, isohexyl, isoheptyl, isooctyl, isononyl and isodecyl.

"$C_2$–$C_{10}$ alkenyl" refers to a straight or branched chain unsaturated hydrocarbon containing 2–10 carbon atoms and at least one double bond. Examples of a $C_2$–$C_{10}$ alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene.

"$C_2$–$C_{10}$ alkynyl" refers to a straight or branched chain unsaturated hydrocarbon containing 2–10 carbon atoms and at least one triple bond. Examples of a $C_2$–$C_{10}$ alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne and 5-decyne.

"$C_1$–$C_4$ alkylene" refers to a $C_1$–$C_4$ alkyl group in which one of the $C_1$–$C_4$ alkyl group's hydrogen atoms has been replaced with a bond. Examples of a $C_1$–$C_4$ alkylene include —$CH_2$—, —$CH_2CH_2$—, —$CH_2CH_2CH_2$— and —$CH_2CH_2CH_2CH_2$—.

"$C_1$–$C_5$ alkylene" refers to a $C_1$–$C_5$ alkyl group in which one of the $C_1$–$C_5$ alkyl group's hydrogen atoms has been replaced with a bond. Examples of a $C_1$–$C_4$ alkylene include —$CH_2$—, —$CH_2CH_2$—, —$CH_2CH_2CH_2$— and—Examples of a $C_1$–$C_4$ alkylene include —$CH_2$—, —$CH_2CH_2$—, —$CH_2CH_2CH_2$—, —$CH_2CH_2CH_2CH_2$— and —$CH_2CH_2CH_2CH_2CH_2$—.

"Alkylhalo" refers to a $C_1$–$C_5$ alkyl group, as defined above, wherein one or more of the $C_1$–$C_5$ alkyl group's hydrogen atoms has been replaced with —F, —Cl, —Br or —I. Representative examples of an alkylhalo group include, but are not limited to —$CH_2F$, —$CCl_3$, —$CF_3$, —$CH_2Cl$, —$CH_2CH_2Br$, —$CH_2CH_2I$, —$CH_2CH_2CH_2F$, —$CH_2CH_2CH_2Cl$, —$CH_2CH_2CH_2CH_2Br$, —$CH_2CH_2CH_2CH_2I$, —$CH_2CH_2CH_2CH_2CH_2Br$, —$CH_2CH_2CH_2CH_2CH_2I$, —$CH_2CH(Br)CH_3$, —$CH_2CH(Cl)CH_2CH_3$, —$CH(F)CH_2CH_3$ and —$C(CH_3)_2(CH_2Cl)$.

"Alkylamino" refers to a $C_1$–$C_4$ alkyl group, as defined above, wherein one or more of the $C_1$–$C_4$ alkyl group's hydrogen atoms has been replaced with —$NH_2$. Representative examples of an alkylamino group include, but are not limited to —$CH_2NH_2$, —$CH_2CH_2NH_2$, —$CH_2CH_2CH_2NH_2$, —$CH_2CH_2CH_2CH_2NH_2$, —$CH_2CH(NH_2)CH_3$, —$CH_2CH(NH_2)CH_2CH_3$, —$CH(NH_2)CH_2CH_3$ and —$C(CH_3)_2(CH_2NH_2)$.

"Aminoalkyl" refers to an —NH group, the nitrogen atom of said group being attached to a $C_1$–$C_4$ alkyl group, as defined above. Representative examples of an aminoalkyl group include, but are not limited to —$NHCH_3$, —$NHCH_2CH_3$, —$NHCH_2CH_2CH_3$, —$NHCH_2CH_2CH_2CH_3$, —$NHCH(CH_3)_2$, —$NHCH_2CH(CH_3)_2$, —$NHCH(CH_3)CH_2CH_3$ and —NH—$C(CH_3)_3$.

"Aminodialkyl" refers to a nitrogen atom which has attached to it two $C_1$–$C_4$ alkyl groups, as defined above. Representative examples of a aminodialkyl group include, but are not limited to, —$N(CH_3)_2$, —$N(CH_2CH_3)(CH_3)$, —$N(CH_2CH_3)_2$, —$N(CH_2CH_3)_2$, —$N(CH_2CH_2CH_2CH_3)_2$, —$N(CH(CH_3)_2)_2$, —$N(CH(CH_3)_2)(CH_3)$, —$N(CH_2CH(CH_3)_2)_2$, —$NH(CH(CH_3)CH_2CH_3)_2$, —$N(C(CH_3)_3)_2$ and —$N(C(CH_3)_3)(CH_3)$.

"Aryl" refers to a phenyl or pyridyl group. Examples of an aryl group include, but are not limited to, phenyl, N-pyridyl, 2-pyridyl, 3-pyridyl and 4-pyridyl. An aryl group can be unsubstituted or substituted with one or more of the following groups:

—$C_1$–$C_5$ alkyl, halo, -alkylhalo, hydroxy, —O—$C_1$–$C_5$ alkyl, —$NH_2$, -aminoalkyl, -aminodialkyl, —COOH, —C(O)O—($C_1$–$C_5$ alkyl), —OC(O)—($C_1$–$C_5$ alkyl), —N-amidoalkyl, —$C(O)NH_2$, -carboxamidoalkyl, or —$NO_2$.

"Arylalkyl" refers to an aryl group, as defined above, wherein one of the aryl group's hydrogen atoms has been replaced with a $C_1$–$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl, "Arylamido" refers to an aryl group, as defined above, wherein one of the aryl group's hydrogen atoms has been replaced with one or more —$C(O)NH_2$ groups. Representative examples of an arylamido group include 2-$C(O)NH_2$-phenyl, 3-$C(O)NH_2$-phenyl, 4-$C(O)NH_2$-phenyl, 2-$C(O)NH_2$-pyridyl, 3-$C(O)NH_2$-pyridyl and 4-$C(O)NH_2$-pyridyl, "Alkylheterocycle" refers to a $C_1$–$C_5$ alkyl group, as defined above, wherein one of the $C_1$–$C_5$ alkyl group's hydrogen atoms has been replaced with a heterocycle. Representative examples of an alkylheterocycle group include, but are not limited to, —$CH_2CH_2$-morpholine, —$CH_2CH_2$-piperidine, —$CH_2CH_2CH_2$-morpholine and —$CH_2CH_2CH_2$-imidazole.

"Alkylamido" refers to a $C_1$–$C_5$ alkyl group, as defined above, wherein one of the $C_1$–$C_5$ alkyl group's hydrogen atoms has been replaced with a —$C(O)NH_2$ group. Representative examples of an alkylamido group include, but are not limited to, —$CH_2C(O)NH_2$, —$CH_2CH_2C(O)NH_2$, —$CH_2CH_2CH_2C(O)NH_2$, —$CH_2CH_2CH_2CH_2C(O)NH_2$, —$CH_2CH_2CH_2CH_2CH_2C(O)NH_2$, —$CH_2CH(C(O)NH_2)CH_3$, —$CH_2CH(C(O)NH_2)CH_2CH_3$, —$CH(C(O)NH_2)CH_2CH_3$ and —$C(CH_3)_2CH_2C(O)NH_2$.

"Alkanol" refers to a $C_1$–$C_5$ alkyl group, as defined above, wherein one of the $C_1$–$C_5$ alkyl group's hydrogen atoms has been replaced with a hydroxyl group. Representative examples of an alkanol group include, but are not limited to, —$CH_2OH$, —$CH_2CH_2OH$, —$CH_2CH_2CH_2OH$, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_2$CH$_3$ and —C(CH$_3$)$_2$CH$_2$OH.

"Alkylcarboxy" refers to a C$_1$–C$_5$ alkyl group, as defined above, wherein one of the C$_1$–C$_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

"N-amidoalkyl" refers to a —NHC(O)— group in which the carbonyl carbon atom of said group is attached to a C$_1$–C$_5$ alkyl group, as defined above. Representative examples of a N-amidoalkyl group include, but are not limited to, —NHC(O)CH$_3$, —NHC(O)CH$_2$CH$_3$, —NHC(O)CH$_2$CH$_2$CH$_3$, —NHC(O)CH$_2$CH$_2$CH$_2$CH$_3$, —NHC(O)CH$_2$CH$_2$CH$_2$CH$_2$CH$_3$, —NHC(O)CH(CH$_3$)$_2$, —NHC(O)CH$_2$CH(CH$_3$)$_2$, —NHC(O)CH(CH$_3$)CH$_2$CH$_3$, —NHC(O)—C(CH$_3$)$_3$ and —NHC(O)CH$_2$C(CH$_3$)$_3$.

"Carboxamidoalkyl" refers to a —C(O)NH— group in which the nitrogen atom of said group is attached to a C$_1$–C$_5$ alkyl group, as defined above. Representative examples of a carboxamidoalkyl group include, but are not limited to, —C(O)NHCH$_3$, —C(O)NHCH$_2$CH$_3$, —C(O)NHCH$_2$CH$_2$CH$_3$, —C(O)NHCH$_2$CH$_2$CH$_2$CH$_3$, —C(O)NHCH$_2$CH$_2$CH$_2$CH$_2$CH$_3$, —C(O)NHCH(CH$_3$)$_2$, —C(O)NHCH$_2$CH(CH$_3$)$_2$, —C(O)NHCH(CH$_3$)CH$_2$CH$_3$, —C(O)NH—C(CH$_3$)$_3$ and —C(O)NHCH$_2$C(CH$_3$)$_3$.

An "Arylene" group is a phenyl group in which one of the phenyl group's hydrogen atoms has been replaced with a bond. An arylene group can be in an ortho, meta, or para configuration and can be unsubstituted or independently substituted with one or more of the following groups: —C$_1$–C$_5$ alkyl, halo, -alkylhalo, hydroxy, —O—C$_1$–C$_5$ alkyl, —NH$_2$, -aminoalkyl, -aminodialkyl, —COOH, —C(O)O—(C$_1$–C$_5$ alkyl), —OC(O)—(C$_1$–C$_5$ alkyl), —N-amidoalkyl, —C(O)NH$_2$, -carboxamidoalkyl or —NO$_2$.

A "C$_3$–C$_8$ Carbocycle" is a non-aromatic, saturated hydrocarbon ring containing 3–8 carbon atoms. Representative examples of a C$_3$–C$_8$ carbocycle include, but are not limited to, cyclopropyl, cyclobutyl, cyclopentyl, cyclohexyl, cycloheptyl and cyclooctyl. A C$_3$–C$_8$ carbocycle can be unsubstituted or independently substituted with one or more of the following groups: —C$_1$–C$_5$ alkyl, halo, -alkylhalo, hydroxy, —O—C$_1$–C$_5$ alkyl, —NH$_2$, -aminoalkyl, -aminodialkyl, —COOH, —C(O)O—(C$_1$–C$_5$ alkyl), —OC(O)—(C$_1$–C$_5$ alkyl), —N-amidoalkyl, —C(O)NH$_2$, -carboxamidoalkyl or —NO$_2$.

"Heterocycle" refers to a 5- to 10-membered aromatic or non-aromatic carbocycle in which 1–4 of the ring carbon atoms have been independently replaced with a N, O or S atom. Representative examples of a heterocycle group include, but are not limited to, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl. A heterocycle group can be unsubstituted or substituted with one or more of the following groups: —C$_1$–C$_5$ alkyl, halo, -alkylhalo, hydroxy, —O—C$_1$–C$_5$ alkyl, —NH$_2$, -aminoalkyl, -aminodialkyl, —COOH, —C(O)O—(C$_1$–C$_5$ alkyl), —OC(O)—(C$_1$–C$_5$ alkyl), —N-amidoalkyl, —C(O)NH$_2$, -carboxamidoalkyl or —NO$_2$.

A "Heterocyclic amine" is a heterocycle, defined above, having 1–4 ring nitrogen atoms. Representative examples of heterocyclic amines include, but are not limited to, piperidinyl, piperazinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, pyridinyl, oxazolyl, benzoxazolyl, thiazolyl, benzthiazolyl, pyrazolyl, triazolyl, benzodiazolyl, benzotriazolyl, pyrimidinyl, isoindolyl, indazolyl and morpholinyl; each of which can be unsubstituted or substituted with one or more of —N—(C$_1$–C$_5$ alkyl), —C(O)—(C$_1$–C$_5$ alkyl), —N—C(O)(C$_1$–C$_4$ alkyl), —O—(C$_1$–C$_5$ alkyl), -halo, -alkylhalo, -alkanol, -alkylamino, -hydroxy, —NO$_2$, —NH$_2$, -aminoalkyl, -aminodialkyl, -heterocyclic amine, —C$_1$–C$_{10}$ alkyl, —C$_2$–C$_{10}$ alkenyl, —C$_2$–C$_{10}$ alkynyl, -aryl, -benzyl, -alkylamido, -alkylcarboxy, —COOH, —C$_1$–C$_5$ alkylene-OC(O)—C$_1$–C$_5$ alkyl, —C$_1$–C$_5$ alkylene-C(O)O—C$_1$–C$_5$ alkyl, or a heterocycle or C$_3$–C$_8$ carbocycle which can be unsubstituted or substituted with one or more of —C$_1$–C$_{10}$ alkyl, —O—(C$_1$–C$_5$ alkyl), -halo, -alkylhalo, -alkanol, -alkylamino, -hydroxy, —NO$_2$ or —NH$_2$.

"Halo" is —F, —Cl, —Br or —I.

A "subject" is a mammal, e.g., a human, mouse, rat, guinea pig, dog, cat, horse, cow, pig, or non-human primate, such as a monkey, chimpanzee, baboon or rhesus.

The invention also includes pharmaceutical compositions comprising an effective amount of an Isoquinoline Derivative and a pharmaceutically acceptable carrier. The invention includes an Isoquinoline Derivative when provided as a pharmaceutically acceptable prodrug, hydrated salt, such as a pharmaceutically acceptable salt, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

An "effective amount" when used in connection an Isoquinoline Derivative is an amount effective for: (a) treating or preventing an inflammatory disease or a reperfusion disease or (b) inhibiting PARS in an in vivo or an in vitro cell.

The following abbreviations are used herein and have the indicated definitions: AcOH is acetic acid, CEP is Cecal Ligation and Puncture, DMEM is Dulbecco's Modified Eagle Medium, DMF is N,N-dimethylformamide, DMSO is dimethylsulfoxide, EtOAc is ethyl acetate, EtOH is ethanol, HEPES is 4-(2-hydroxyethyl)-1-piperazineethanesulfonic acid, HPLC is high pressure liquid chromatography, LPS is lipopolysaccharide, MeCN is acetonitrile, MeOH is methanol, MS is mass spectrometry, Ms is mesyl (methanesulfonyl), $NEt_3$ is triethylamine, NMR is nuclear magnetic resonance, PBS is phosphate-buffered saline (pH 7.4), PARS is poly(ADP-ribose)synthetase, Py is pyridine, SDS is dodecyl sulfate (sodium salt), STZ is streptozotocin, TCA is tricholoroacetic acid, Tf is triflyl (trifluoromethanesulfonyl), TFA is trifluoroacetic acid, THF is tetrahydrofuran; TLC is thin-layer chromatography, TNF is tumor necrosis factor, TRIS is Tris(hydroxymethyl)aminomethane and Ts is tosyl (p-toluenesulfonyl).

Methods for Using Isoquinoline Derivatives

The invention also includes methods for inhibiting PARS in a cell. PARS, which is also known as poly(ADP-ribose) synthetase, PARP ((poly(ADP-ribose) polymerase, EC 2.4.99) and ADP-ribosyltransferase (ADPRT, EC 2.4.2.30), is a nuclear enzyme that catalyzes a transfer of the ADP ribose moiety of NAD+ to an acceptor protein.

In one embodiment the method comprises contacting a cell with an Isoquinoline Derivative in an amount sufficient to inhibit PARS in the cell. In general, any cell having, or capable of having, PARS activity or capable of expressing PARS can be used. The cell can be provided in any form. For example, the cell can be provided in vitro, ex vivo, or in vivo. PARS activity can be measured using any method known in the art, e.g., methods as described in Banasik et al., J. Biol. Chem. 267:1569–75 (1991). Illustrative examples of cells capable of expressing PARS include, but are not limited to muscle, bone, gum, nerve, brain, liver, kidney, pancreas, lung, heart, bladder, stomach, colon, rectal, small intestine, skin, esophageal, eye, larynx, uterine, ovarian, prostate, tendon, bone marrow, blood, lymph, testicular, vaginal and neoplastic cells.

Also provided in the invention is a method for inhibiting, preventing, or treating inflammation or an inflammatory disease in a subject. The inflammation can be associated with an inflammatory disease. Inflammatory diseases can arise where there is an inflammation of the body tissue. These include local inflammatory responses and systemic inflammation. Examples of such diseases include: organ transplant rejection; reoxygenation injury resulting from organ transplantation (see Grupp et al. J. Mol. Cell Cardiol. 31:297–303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoinimune encephalitis; autoimmune diseases including Type I and Type II diabetes mellitus; diabetic complications, including, but not limited to, diabetic cataract, glaucoma, retinopathy, nephropathy, such as microaluminuria and progressive diabetic nephropathy, polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication, such as an infection, a shin spot, a candidal infection or necrobiosis lipoidica diabeticorum; immune-complex vasculitis, systemic lupus erythematosus (SLE); inflammatory diseases of the heart such as cardiomyopathy, ischemic heart disease hypercholesterolemia, and atherosclerosis; as well as various other diseases that can have significant inflammatory components, including preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

In one embodiment, a reoxygenation injury resulting from organ transplantation occurs during the organ transplantation.

The invention also includes methods for treating, preventing, or otherwise inhibiting reperfusion disease in a subject in need of treatment, prevention, or inhibition thereof. The method comprises administering an Isoquinoline Derivative in an amount sufficient to treat, prevent or inhibit reperfusion disease in the subject. Reperfusion refers to the process whereby blood flow in the blood vessels is resumed following ischemia, such as occurs following constriction or obstructionof the vessel. Reperfusion disease can result following a naturally occurring episode, such as a myocardial infarction, stroke, or during a surgical procedure where blood flow in vessels is intentionally or unintentionally blocked.

In some embodiments, the subject is administered an effective amount of an Isoquinoline Derivative.

The invention also includes pharmaceutical compositions useful for treating or preventing an inflammatory disease or a reperfusion disease, or for inhibiting PARS activity, or more than one of these activities. The compositions can be suitable for internal use and comprise an effective amount of an Isoquinoline Derivative and a pharmaceutically acceptable carrier. The Isoquinoline Derivatives are especially useful in that they demonstrate very low peripheral toxicity or, no peripheral toxicity.

The Isoquinoline Derivatives can be administered in amounts that are sufficient to treat or prevent an inflammatory disease or a reperfusion disease and/or prevent the development thereof in subjects.

Administration of the Isoquinoline Derivatives can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or thelike, preferably in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising an Isoquinoline Derivative and a pharmaceutically acceptable carrier, such as a) a diluent, e.g., lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone; if desired d) a disintegrant, e.g., starches, agar, methyl cellulose, bentonite, xanthan gum, algiic acid or its sodium salt, or effervescent mixtures; and/or e) absorbent, colorant, flavorant and sweetener.

Liquid, particularly injectable, compositions can, for example, be prepared by dissolution, dispersion, etc. For example, the Isoquinoline Derivative is dissolved in or mixed with a pharmaceutically acceptable solvent such as, for example, water, saline, aqueous dextrose, glycerol, ethanol, and the like, to thereby form an injectable isotonic solution or suspension.

The Isoquinoline Derivatives can be also formulated as a suppository that can be prepared from fatty emulsions or suspensions; using polyalkylene glycols such as propylene glycol, as the carrier.

The Isoquinoline Derivatives can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Isoquinoline Derivatives can also be delivered by the use of monoclonal antibodies as individual carriers to which the Isoquinoline Derivative molecules are coupled. The Isoquinoline Derivatives can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Isoquinoline Derivatives can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

One embodiment for parenteral administration employs the implantation of a slow-release or sustained-released system, according to U.S. Pat. No. 3,710,795, incorporated herein by reference.

The compositions can be sterilized or contain non-toxic amounts of adjuvants, such as preserving, stabilizing, wetting or emulsifying agents, solution promoters, salts for regulating the osmotic pressure pH buffering agents, and other substances, including, but not limited to, sodium acetate or triethanolamine oleate. In addition, they can also contain other therapeutically valuable substances.

Compositions can be prepared according to conventional mixing, granulating or coating methods, respectively, and the present pharmaceutical compositions can contain from about 0.1% to about 99%, preferably from about 1% to about 70% of the Isoquinoline Derivative by weight or volume.

The dosage regimen utilizing the Isoquinoline Derivative is selected in accordance with a variety of factors including type, species, age, weight, sex and medical condition of the patient; the severity of the condition to be treated; the route of administration; the renal or hepatic function of the patient; and the particular Isoquinoline Derivative employed. An physician or veterinarian of ordinary skill in the art can readily determine and prescribe the effective amount of the drug required to prevent, counter or arrest the progress of the condition.

Effective dosage amounts of the present invention, when used for the indicated effects, range from about 0.05 to about 1000 mg of Isoquinoline Derivative per day. Compositions for in vivo or in vitro use can contain about 0.5, 1.0, 2.5, 5.0, 10.0, 15.0, 25.0, 50.0, 100.0, 250.0, 500.0 or 1000.0 mg of Isoquinoline Derivative. In one embodiment, the compositions are in the form of a tablet that can be scored. Effective plasma levels of the Isoquinoline Derivatives can range from about 0.002 mg to about 50 mg per kg of body weight per day.

Isoquinoline Derivatives can be administered in a single daily dose, or the total daily dosage can beadministered in divided doses of two, three or four times daily. Furthermore, Isoquinoline Derivatives can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of Isoquinoline Derivative ranges from about 0.1% to about 15%, w/w or w/v.

Methods for Making the Isoquinoline Derivatives

Examples of synthetic pathways useful for making Isoquinoline Derivatives are set forth in the Examples below and generalized in Schemes 1–9.

Methods useful for making Isoquinoline Derivatives of formula (I) wherein X is —$CH_2$— and $R_5$ is O are illustrated below in Scheme 1.

Scheme 1
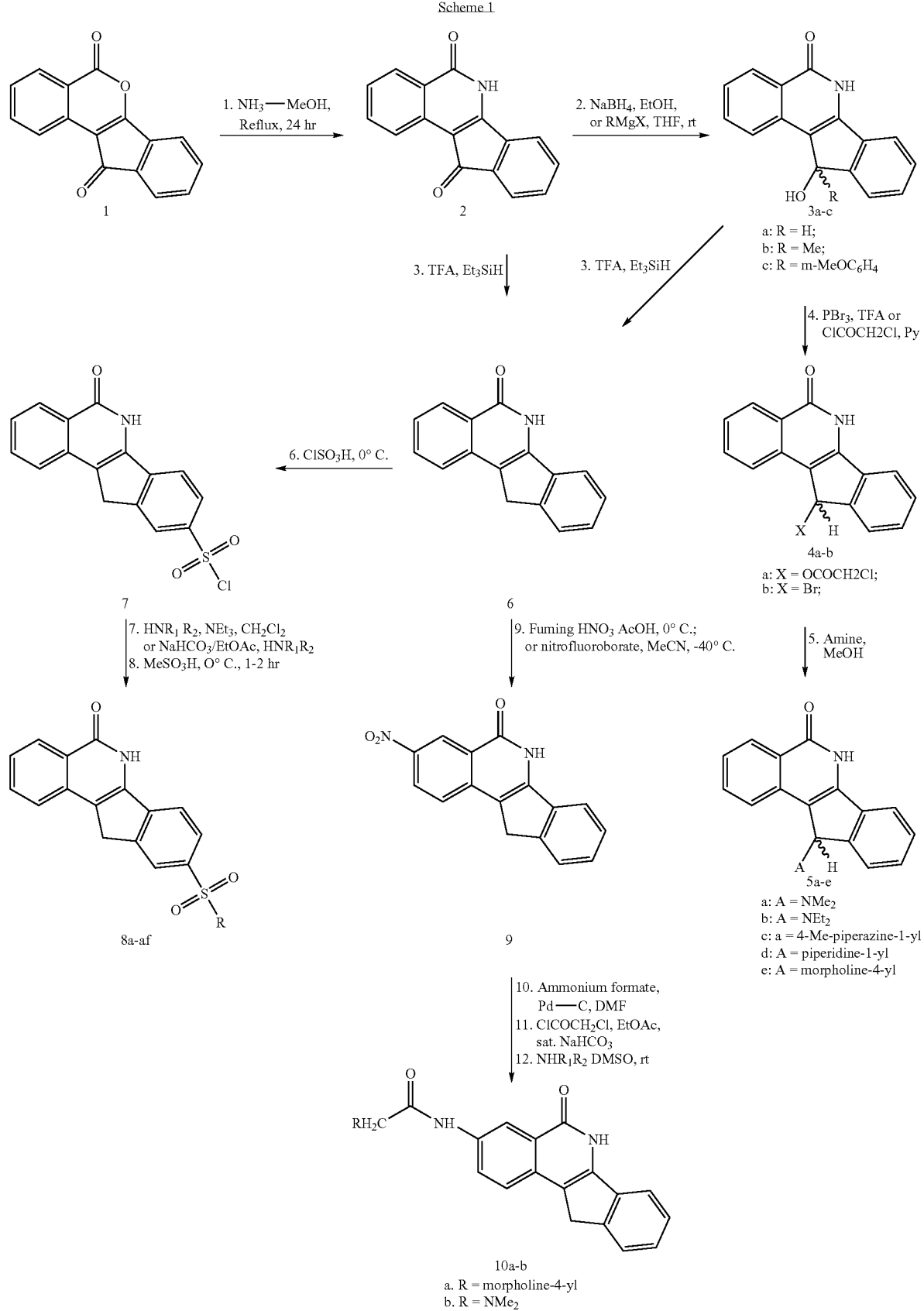

wherein compounds 8a–8af are as follows:

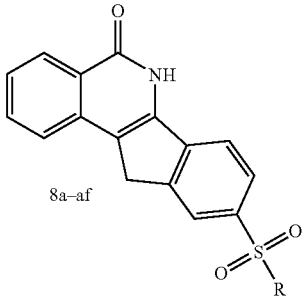

a. R = 4-Methyl-piperazine-1-yl
b. R = 4-CH$_2$CO$_2$Me-piperazine-1-yl
c. R = 4-CH$_2$CH$_2$OH-piperazine-1-yl
d. R = imidazole-1-yl
e. R = L-prolinol
f. R = morpholine-4-yl
g. R = NHCH$_2$CH$_2$NMe$_2$
h. R = NHCH$_2$CH$_2$-piperidine-1-yl
i. R = NHCH$_2$CH$_2$N-(pyridine-2-yl)
j. R = NHCH$_2$CH$_2$-morpholine-4-yl
k. R = NHCH$_2$CH$_2$-(2-N—Me-tetrahydropyrrolidine-1-yl
l. R = NHCH$_2$CH$_2$CH$_2$-morpholine-4-yl
m. R = NHCH$_2$CH$_2$CH$_2$-(tetrahydropyrrolidine-1-yl)
n. R = NHCH$_2$CH$_2$CH$_2$-imidazole-1-yl
o. R = NHCH$_2$CH$_2$CH$_2$-(4-methylpiperazine-1-yl)
p. R = N(CH$_2$CH$_2$NEt$_2$)$_2$
q. R = —N(CH$_2$CH$_2$NMe$_2$)$_2$
r. R = —N(CH$_2$CH$_2$OH)$_2$
s. R = —NHCH$_2$CH$_2$CN
t. R = —NHC(NH)NH$_2$
u. R = —NH[4-(1,2,4-triazole)]
v. R = —NH[4-(N-morpholine)phenyl]
w. R = —NHCH$_2$CH$_2$(4-N-benzylpiperidine)
x. R = —NHCH$_2$CH$_2$(2-thienyl)
y. R = —NH[1-(4-azabenzimidazole)]
z. R = —NH[1-(4-(2'-pyridyl)piperazine)]
aa. R = —NHCH$_2$CH$_2$N[CH$_2$CH$_2$OH]$_2$
ab. R = —NH[1-(4-benzylpiperazine)]
ac. R = —NH$_2$
ad. R = —NHCH$_2$CH$_2$Ph
ae. R = —NHCH$_2$CH$_2$[4-OMe(phenyl)]
af. R = —NHC(O)(N-morpholine)

5,6-dihydro-5,11-diketo-11H-isoquinoline (2) was prepared by reacting compound 1 (Aldrich Chemical, Milwaukee, Wis.) with ammonia in methanol.

(±) 11-hydroxy-5,6-dihydro-5-oxo-11H-indeno[1,2-c]isoquinoline (3a) was prepared by reacting 2 with NaBH$_4$ in ethanol.

(±) 11-hydroxy-11-methyl-5,6-dihydro-5-oxo-11H-isoquinoline (3b) was prepared by reacting 2 with MeMgI.

(±) 11-hydroxy-11-(m-methoxyphenyl)-5,6-dihydro-5-oxo-11H-indeno[1,2-c]isoquinoline (3c) was prepared from 2 using m-MeO—C$_6$H$_4$MgI.

(±) 11-N,N-dimethylamino-5,6-dihydro-5-oxo-11H-indeno[1,2-c]isoquinoline (5a) was prepared from 3a using chloroacetylchloride followed by reacting with dimethylamine. Similarly prepared are: (±) 11-N,N-diethylamino-5,6-dihydro-5-oxo-11H-indeno[1,2-c]isoquinoline (5b), (±) 11-N-(piperidino-1-yl)-5,6-dihydro-5-oxo-11H-indeno[1,2-c]isoquinoline (5d), (±) 11-N-(4-methylpiperazino-1-yl)-5,6-dihydro-5-oxo-11H-indeno[1,2-c]isoquinoline (5c), (±) 11-N-(morpholino-4-yl)-5,6-dihydro-5-oxo-11H-isoquinoline (5e). (±) 11-N-(morpholino-4-yl)-5,6-dihydro-5-oxo-11H-indeno[1,2-c]isoquinoline (5e) was also prepared from (±) 11-bromo-5,6-dihydro-5-oxo-11H-indeno[1,2-c]isoquinoline (4b).

5,6-Dihydro-5-oxo-11H-indeno-[1,2-c]isoquinoline (6) is prepared by reduction of 5,6-dihydro-5,1-diketo-11H-isoquinoline (2) or (±) 11-hydroxy-5,6-dihydro-5-oxo-11H-isoquinoline (3a) using CF$_3$COOH/triethylsilane. 9–Chlorosulphonyl-5,6-dihydro-5-oxo-11H-indeno-[1,2-c]isoquinoline (7) was prepared by chlorosulfonation of 5,6-dihydro-5-oxo-11H-indeno-[1,2-c]isoquinoline (6). 9-[N-(4-methylpiperazine-1-yl)sulphonyl]-5,6-dihydro-5-oxo-11H-indeno-[1,2-c]isoquinoline (8a) was prepared from 9-chlorosulphonyl-5,6-dihydro-5-oxo-11H-indeno-[1,2-c]isoquinoline (7), and N-methylpiperazine. Similarly prepared are: 9-[N-(4-carbomethoxymethylenepiperazino-1-yl)sulphonyl]-5,6-dihydro-5-oxo-11H-indeno-[1,2-c]isoquinoline (8b), 9-[N-4-(2-hydroxyethylpiperazino-1-yl)-sulphonyl]-5,6-dihydro-5-oxo-11H-indeno-[1,2-c]isoquinoline (8c), 9-[N-(imidazolo-1-yl)sulphonyl]-5,6-dihydro-5-oxo-11H-isoquinoline (8d), 9-[N-(2-hydroxyprolinyl)sulphonyl]-5,6-dihydro-5-oxo-11H-indeno[2-c]isoquinoline (8e), 9-[N-morpholinesulphonyl]-5,6-dihydro-5-oxo-11H-indeno-[1,2-c]isoquinoline (8f), 9-[N-(2-[N,N-dimethylamino]ethyl)-aminosulphonyl]-5,6-dihydro-5-oxo-11H-indeno[1,2-c]isoquinoline (8g), 9-[N-(2-[piperidino-1-yl]ethyl)-aminosulphonyl]-5,6-dihydro-5-oxo-11H-indeno[1,2-c]isoquinoline (8h), 9-[N-(2-(pyridino-2-yl)-ethyl)-aminosulphonyl]-5,6-dihydro-5-oxo-11H-indeno[1,2-c]isoquinoline (8i), 9-[N-(2-[morpholino-4-yl]ethyl)-aminosulphonyl]-5,6-dihydro-5-oxo-11H-indeno[1,2-c]isoquinoline (8j), 9-[N-(2-[N-methyltetrahydropyrrolidino-1-yl]ethyl)aminosulphonyl]-5,6-dihydro-5-oxo-11H-indeno-[1,2-c]isoquinoline (8k), 9-[N-(3-[morpholino-4-yl]propyl)-aminosulphonyl]-5,6-dihydro-5-oxo-11H-indeno-[1,2-c]isoquinoline (8l), 9-[N-(3-[tetrahydropyrrolodino-1-yl]propyl)aminosulphonyl]-5,6-dihydro-5-oxo-11H-indeno-[1,2-c]isoquinoline (8m), 9-[N-(3-[imidazolo-1-yl]propyl)-aminosulphonyl]-5,6-dihydro-5-oxo-11H-indeno-[1,2-c]isoquinoline (8n), 9-[N-[3-(4-methylpiperazino-1-yl]propyl)-aminosulphonyl]-5,6-dihydro-5-oxo-11H-indeno-[1,2-c]isoquinoline (8o), 9-[N,N-di-(2-[N,N-diethylamino]ethyl)-aminosulphonyl]-5,6-dihydro-5-oxo-11H-indeno-[1,2-c]isoquinoline (8p), 9-[N,N-di-(2-[N,N-dimethylamino]ethyl)-aminosulphonyl]-5,6-dihydro-5-oxo-11H-indeno-[1,2-c]isoquinoline (8q), and 9-[N,N-di-(2-[N,N-dihydroxyethylamino]ethyl)-aminosulphonyl]-5,6-dihydro-5-oxo-11H-indeno-[1,2-c]isoquinoline (8r).

Compounds 8s–8af can be prepared using the methods described above for making compounds of 8a–8r, using appropriate amine intermediates.

Scheme 2 illustrates a method useful for making terminal carboxylic acid compounds of formulas 8ag–8ao. This method comprises reacting sulfonyl chloride 7 with the alkyl ester of an amino acid in the presence of a base, preferably triethyamine, to provide an intermediate terminal carboxylic acid alkyl ester, which is then hydrolyzed using a base such as sodium hydroxide to provide the corresponding terminal carboxylic acid.

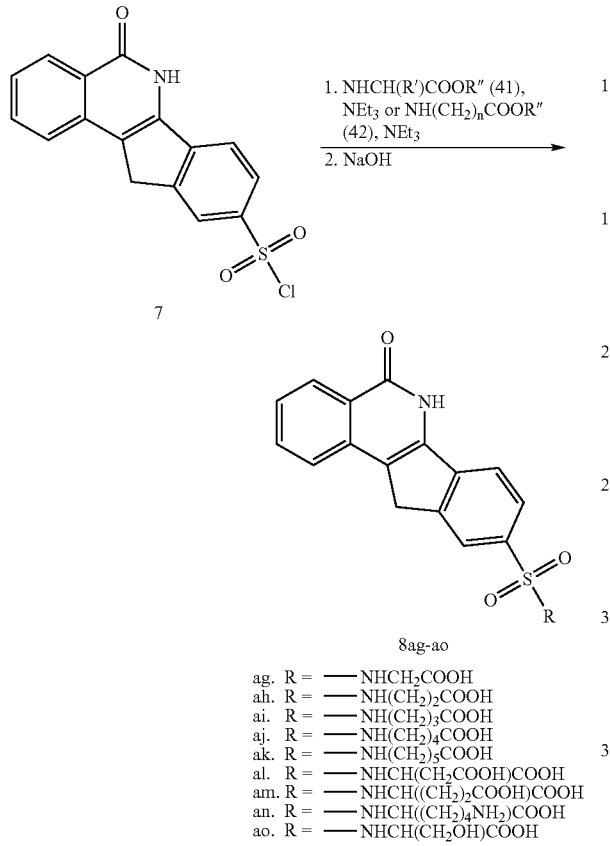

wherein
R' is -alkylcarboxy, -alkylamino or -alkanol;
R" is —C$_1$–C$_6$ alkyl; and
n is an integer ranging from 1 to 6.

General Procedure for making 9-sulfonamido carboxylic acid derivatives

Preparation of 9-sulfonamido carboxylic acid ester

To a 0.5M solution of an ester of formula 41 or 42 in CH$_2$Cl$_2$ is added compound 7 (1.0 eq) and the resulting mixture is stirred for 5 minutes. Triethylamine (about 5 eq) is then added and the resulting reaction is stirred at room temperature and monitored using TLC or HPLC until complete. The reaction mixture is filtered, the solid is washed using MeOH to provide the intermediate 9-sulfonamido carboxylic acid ester which can be used without further purification.

Ester Hydrolysis

To an approximately 0.5M solution of a 9-sulfonamide carboxylic acid ester in ethanol is added about 3.0 N aqueous sodium hydroxide (about 5.0 eq) and the resulting reaction is refluxed if necessary and monitored using TLC or HPLC until completion. The reaction mixture is neutralized to about pH 7.0 using about 1.0 N HCl and the neutralized reaction mixture is extracted twice using EtOAc. The combined EtOAc layers are washed sequentially with water and saturated aqueous sodium chloride, then dried over sodium sulfate and concentrated in vacuo to afford a crude residue which is purified using flash column chromatography to provide the desired 9-sulfonamide carboxylic acid compound.

Acid hydrolysis with neat TFA can be useful where the sulfonamide has a t-butyl ester group.

In another embodiment, illustrated below in Scheme 3, Isoquinoline Derivatives of general formula 13 can be made by a method comprising contacting a compound of formula 11 and a compound of formula 12 in the presence of a base for a time and at a temperature sufficient to make a compound of formula 13.

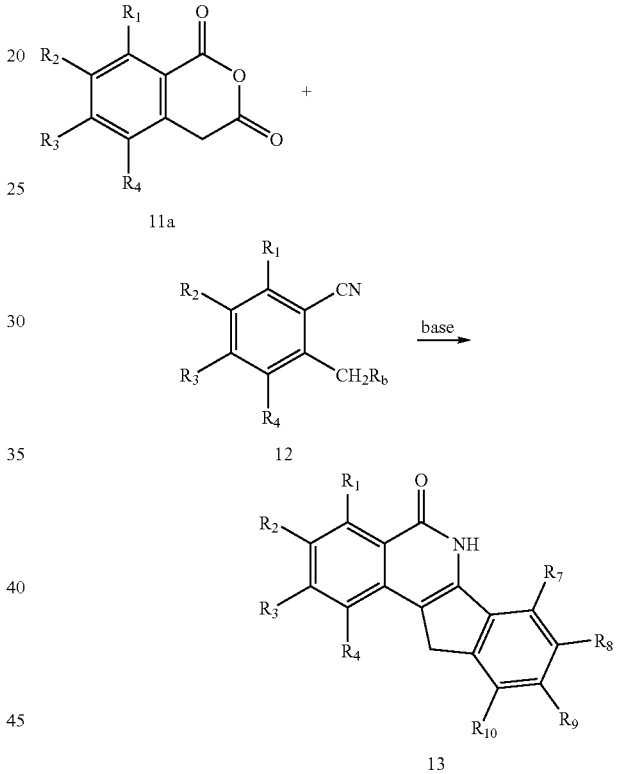

wherein
R$_1$–R$_4$ and R$_7$–R$_{10}$ are as defined above for formula (I); and
R$_b$ is —Cl, —Br, —I, —OMs, —OTs or —OTf.

In one embodiment, R$_b$ is —Br.

In another embodiment, R$_b$ and R$_d$ are both —Br.

In one embodiment about 0.1 to about 10 equivalents of a compound of Formula 12 are used per about 1 equivalent of a compound of Formula 11.

In another embodiment about 0.5 to about 5 equivalents of a compound of Formula 12 are used per about 1 equivalent of a compound of Formula 11.

In still another embodiment, about 1 to about 2 equivalents of a compound of Formula 12 are used per about 1 equivalent of a compound of Formula 11.

In one embodiment about 1 to about 10 equivalents of base are used per about 1 equivalent of a compound of Formula 11.

In another embodiment about 3 to about 7 equivalents of base are used per about 1 equivalent of a compound of Formula 11.

In a yet another embodiment about 5 to about 6 equivalents of base are used per about 1 equivalent of a compound of Formula 11.

Suitable bases for use in the method of Scheme 3 are organic bases such as triethylamine, diisopropylamine, diisopropylethylamine, pyridine, lutidine and imidazole; and inorganic bases such as alkali metal carbonates, including sodium carbonate, potassium carbonate and cesium carbonate.

In one embodiment, the base is triethylamine.

In another embodiment, the base is potassium carbonate.

The method of Scheme 3 can be carried out in the presence of a solvent., such as acetonitrile, methylene chloride, chloroform, THF, DMF, DMSO, ethyl acetate, acetone, benzene, diethyl ether, water or mixtures thereof.

In one embodiment, the solvent is acetonitrile.

In another embodiment, the solvent is DMF.

In still another embodiment, where the solvent is not water, the solvent is substantially anhydrous, i.e., comprises less than about 1% water.

In one embodiment, the method of Scheme 3 is carried out for a time of about 0.5 hours to about 48 hours.

In another embodiment the method of Scheme 3 is carried out for a time of about 3 hours to about 36 hours.

In still another embodiment the method of Scheme 3 is carried out for a time of about 8 hours to about 24 hours.

In yet another embodiment the method of Scheme 3 is carried out for a time of about 15 hours to about 20 hours.

In a further embodiment, the method of Scheme 3 is carried out at a temperature of about 0° C. to about 200° C.

In another embodiment, the method of Scheme 3 is carried out at a temperature of about 25° C. to about 150° C.

In yet another embodiment, the method of Scheme 3 is carried out at a temperature of about 50° C. to about 100° C.

General Procedure for the Preparation of Compounds of Formula 13

To a solution of a homophthalic anhydride of formula 11 (about 1 equivalent) in a suitable solvent, such as acetonitrile, is added a compound of Formula 12 (about 1 to about 2 eq) followed by a suitable base, such as triethylamine (about 1 to about 5 eq). The resulting reaction is reaction is allowed to stir for about 1 hour, at which time a colored precipitate appears. The reaction is then heated at reflux for about 20 hours, cooled to room temperature and filtered. The collected solid is washed using acetonitrile and dried under vacuum to provide a compound of Formula 13.

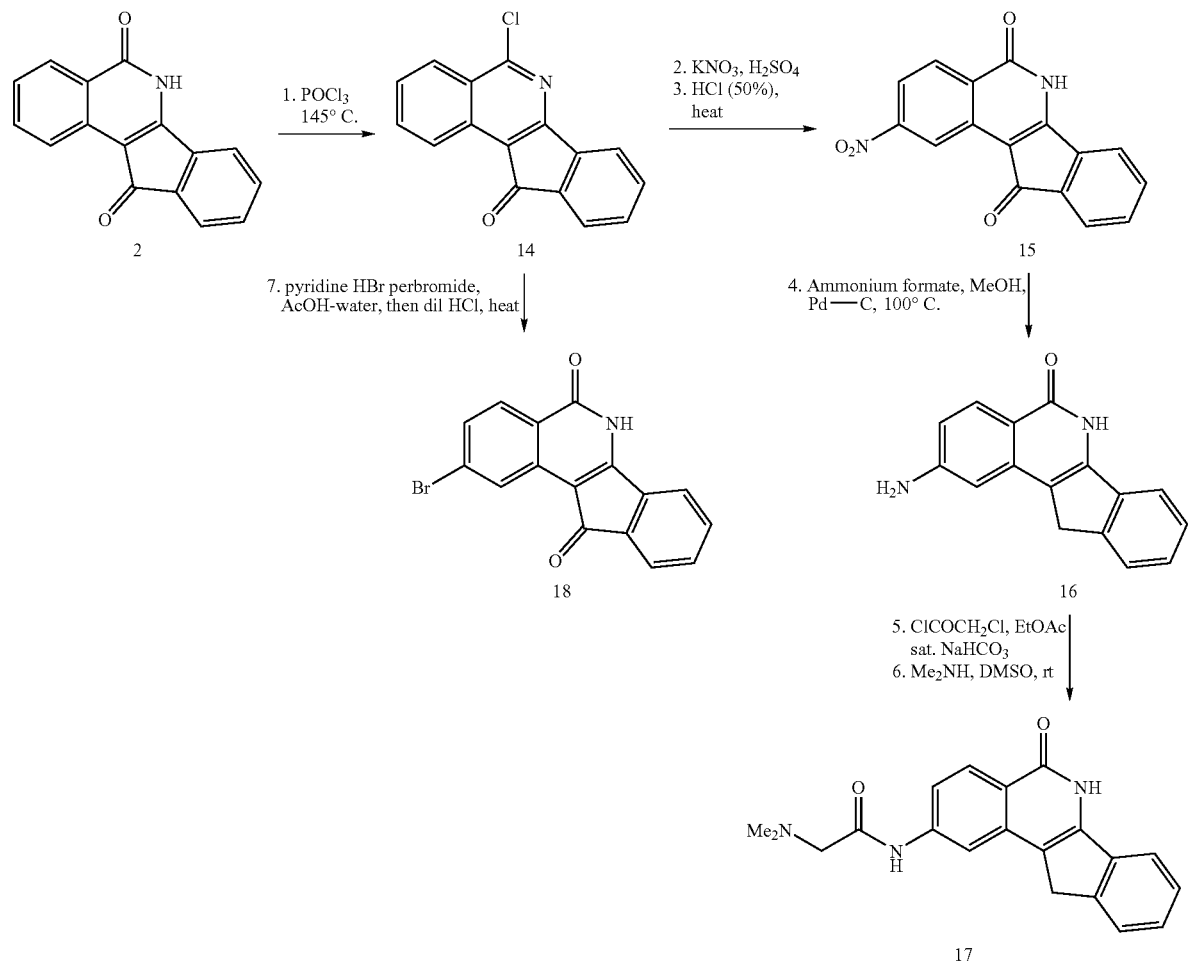

The amide derivative 2-dimethylamino-N-(5-oxo-5,11-dihydro-6H-indeno[1,2-c]isoquinolin-2-yl)-acetamide (17) was prepared from 5-chloro-11H-indeno[1,2-c]isoquinoline (14). Compound 14 was subjected to nitration to provide nitro compound 15, which was reduced using ammonium formate to provide amine 16, which was derivatized to acetamide 17. and followed by amination of the chloroacetamide intermediate. 2-bromo-5,6-dihydro-5-oxo-11H-indeno[1,2-c]isoquinoline (18) was prepared by bromination of Compound 14.

Scheme 5 illustrates methods useful for making oxygen-substituted Isoquinoline Derivatives of formula (I).

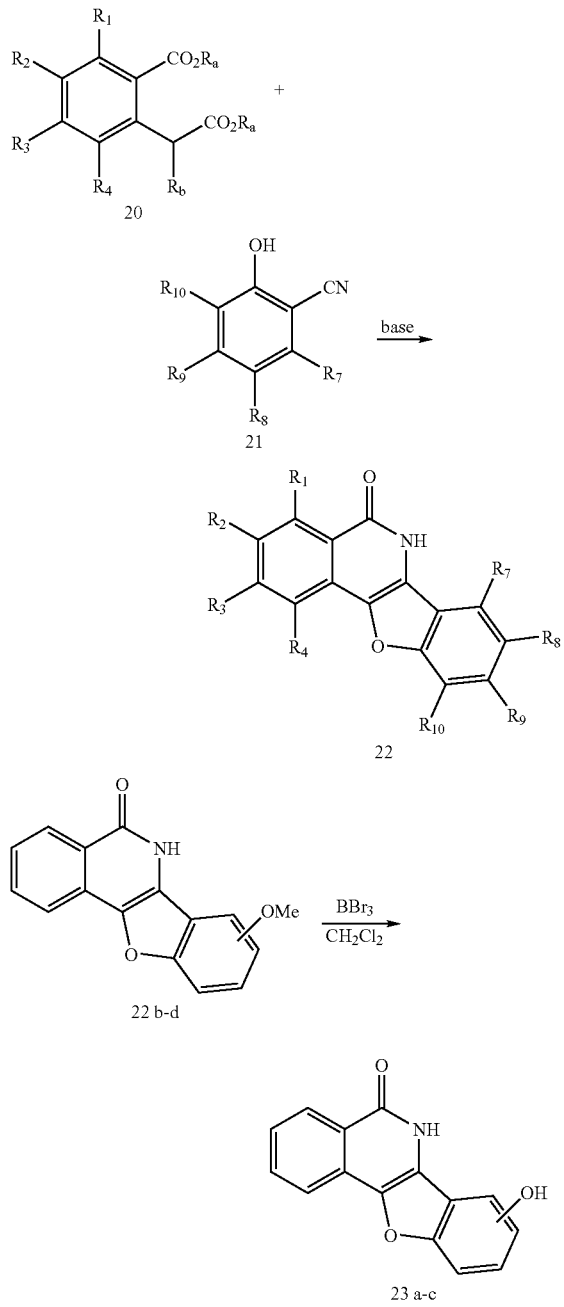

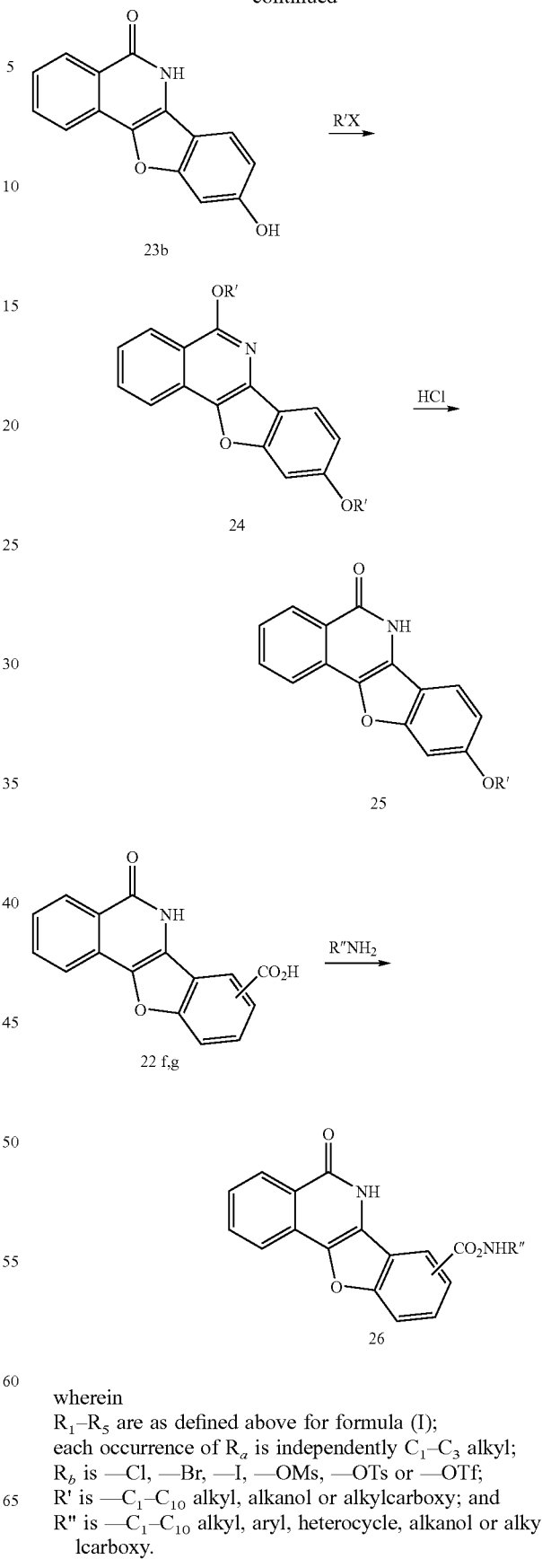

wherein
$R_1$–$R_5$ are as defined above for formula (I);
each occurrence of $R_a$ is independently $C_1$–$C_3$ alkyl;
$R_b$ is —Cl, —Br, —I, —OMs, —OTs or —OTf;
R' is —$C_1$–$C_{10}$ alkyl, alkanol or alkylcarboxy; and
R" is —$C_1$–$C_{10}$ alkyl, aryl, heterocycle, alkanol or alkylcarboxy.

In one embodiment, $R_a$ is methyl.

In another embodiment, $R_b$ is —Br

In another embodiment, illustrated above in Scheme 5, Isoquinoline Derivatives of formula 22 can be made by a method comprising contacting a compound of formula 20 and a compound of formula 21 in the presence of a base for a time and at a temperature sufficient to make a compound of formula 22.

In one embodiment about 0.1 to about 10 equivalents of a compound of Formula 20 are used per about 1 equivalent of a compound of Formula 21.

In another embodiment about 0.5 to about 5 equivalents of a compound of Formula 20 are used per about 1 equivalent of a compound of Formula 21.

In still another embodiment, about 1 to about 2 equivalents of a compound of Formula 20 are used per about 1 equivalent of a compound of Formula 21.

In one embodiment about 1 to about 10 equivalents of base are used per about 1 equivalent of a compound of Formula 21.

In another embodiment about 3 to about 7 equivalents of base are used per about 1 equivalent of a compound of Formula 21.

In a yet another embodiment about 5 to about 6 equivalents of base are used per about 1 equivalent of a compound of Formula 21.

Suitable bases for use in the method are organic bases such as triethylamine, diisopropylamine, diisopropylethylamine, pyridine, lutidine and imidazole; and inorganic bases such as alkali metal carbonates such as sodium carbonate, potassium carbonate and cesium carbonate.

In one embodiment, the base is potassium carbonate.

In another embodiment, the base is triethylamine.

The method can be carried out in the presence of a solvent, such as acetonitrile, methylene chloride, chloroform, THF, DMF, DMSO, ethyl acetate, acetone, benzene, diethyl ether, water or mixtures thereof.

In one embodiment, the solvent is DMF.

In another embodiment, the solvent is acetonitrile.

In still another embodiment, the solvent is substantially anhydrous, i.e., comprises less than about 1% water.

In one embodiment, the method is carried out for a time of about 1 hour to about 96 hours.

In another embodiment the method is carried out for a time of about 18 hours to about 72 hours.

In yet another embodiment the method is carried out for a time of about 24 hours to about 48 hours.

In one embodiment, the method is carried out at a temperature of about 25° C. to about 200° C.

In another embodiment, the method is carried out at a temperature of about 50° C. to about 150° C.

In still another embodiment, the method is carried out at a temperature of about 75° C. to about 125° C.

Scheme 6 illustrates methods useful for making nitrogen-substituted Isoquinoline Derivatives of the invention.

Scheme 6

In an alternate embodiment, illustrated below in Scheme 7, nitrogen-substituted Isoquinoline Derivatives of general formula 37 can be made by a method comprising contacting a compound of formula 36 and a compound of formula 11a or formula 20 in the presence of a base for a time and at a temperature sufficient to make a compound of formula 37.

Scheme 7

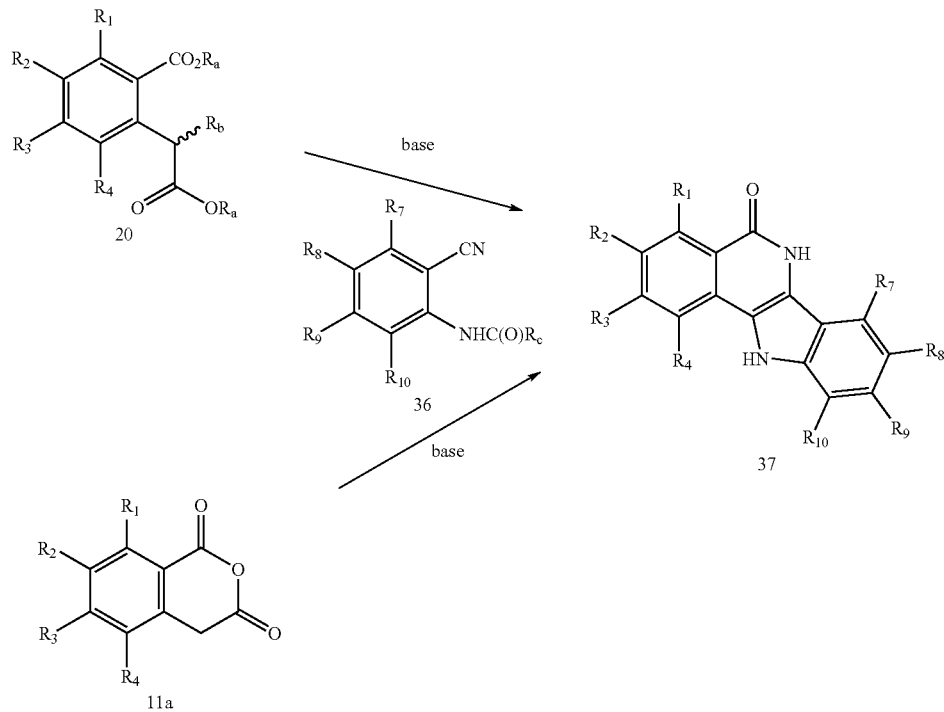

wherein
$R_1$–$R_4$ and $R_7$–$R_{10}$ are as defined above for formula (I);
each occurrence of $R_a$ is independently $C_1$–$C_3$ alkyl;
$R_b$ is —Cl, —Br, —I, —OMs, —OTs or —OTf; and
$R_c$ is $C_1$–$C_3$ alkyl.

In one embodiment, $R_a$ is methyl.
In another embodiment, $R_b$ is —Br.
In a further embodiment, $R_a$ is methyl and $R_b$ is —Br.
In still another embodiment, $R_c$ is methyl.
In one embodiment about 0.1 to about 10 equivalents of a compound of Formula 11a are used per about 1 equivalent of a compound of Formula 36.
In another embodiment about 0.5 to about 5 equivalents of a compound of Formula 11a are used per about 1 equivalent of a compound of Formula 36.
In still another embodiment, about 1 to about 2 equivalents of a compound of Formula 11a are used per about 1 equivalent of a compound of Formula 36.
In one embodiment about 0.1 to about 10 equivalents of a compound of Formula 20 are used per about 1 equivalent of a compound of Formula 36.
In another embodiment about 0.5 to about 5 equivalents of a compound of Formula 20 are used per about 1 equivalent of a compound of Formula 36.
In still another embodiment, about 1 to about 2 equivalents of a compound of Formula 20 are used per about 1 equivalent of a compound of Formula 36.
In one embodiment about 1 to about 10 equivalents of base are used per about 1 equivalent of a compound of Formula 36.
In another embodiment about 3 to about 7 equivalents of base are used per about 1 equivalent of a compound of Formula 11.

In a yet another embodiment about 5 to about 6 equivalents of base are used per about 1 equivalent of a compound of Formula 11.
Suitable bases for use in the method of Scheme 7 are organic bases such as triethylamine, diisopropylamine, diisopropylethylamine, pyridine, lutidine and imidazole; and inorganic bases such as alkali metal carbonates such as sodium carbonate, potassium carbonate and cesium carbonate.
In one embodiment, the base is potassium carbonate.
In another embodiment, the base is triethylamine.
The method of Scheme 7 can be carried out in the presence of a solvent, such as acetonitrile, methylene chloride, chloroform, THF, DMF, DMSO, ethyl acetate, acetone, benzene, diethyl ether, water or mixtures thereof.
In one embodiment, the solvent is DMF.
In another embodiment, the solvent is acetonitrile.
In still another embodiment, the solvent is substantially anhydrous, i.e., comprises less than about 1% water.
In one embodiment, the method of Scheme 7 is carried out for a time of about 1 hour to about 96 hours.
In another embodiment the method of Scheme 7 is carried out for a time of about 18 hours to about 72 hours.
In yet another embodiment the method of Scheme 7 is carried out for a time of about 24 hours to about 48 hours.
In one embodiment, the method of Scheme 7 is carried out at a temperature of about 25° C. to about 200° C.
In another embodiment, the method of Scheme 7 is carried out at a temperature of about 50° C. to about 150° C.
In still another embodiment, the method of Scheme 7 is carried out at a temperature of about 75° C. to about 125° C.

General Procedure for the Preparation of Compounds of Formula 37

From a homophthalate:

To a solution of a homophthalate of Formula 20 (about 1 eq) and an N-acylanthranilonitrile of Formula 36 (about 1 to about 2 eq) in a solvent such as DMF, under inert atmosphere, is added a base (about 5 eq), such as potassium carbonate and the reaction is allowed to stir for about 48 hours at about 100° C., then cooled to room temperature. The reaction mixture is then poured into about 1 N sodium hydroxide and the resulting solution is extracted with EtOAc. The EtOAc layer is washed sequentially with about 1 N HCl, saturated aqueous sodium chloride, dried over sodium sulfate, filtered and concentrated in vacuo. The resulting residue is dissolved using warming in toluene and the resulting solution is cooled to room temperature and precipitated using hexanes. The solid precipitate is filtered, washed using hexanes and dried in a vacuum oven at 50° C. for 72 h to provide a Compound of Formula 36.

The synthesis of phenyl amide 36, which is a useful intermediate in Scheme 7, is described below in Scheme 8. In this procedure, the amine group of a cyanoaniline compound of formula 38 is acylated using an acyl chloride or an anhydride in the presence of a base.

Scheme 8

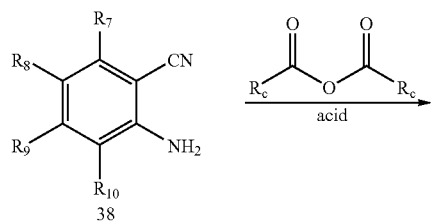

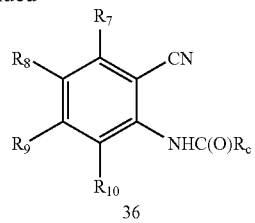

wherein $R_7$–$R_{10}$ are as defined above for formula (I); and $R_c$ is $C_1$–$C_3$ alkyl.

Suitable acids for use in the method of Scheme 8 include, but are not limited to, sulfuric acid and phosphoric acid.

In one embodiment, the acid is sulfuric acid.

In another embodiment, $R_c$ is methyl.

The method of Scheme 8 can be carried out in the presence of a solvent, including, but not limited to, acetonitrile, methylene chloride, chloroform, THF, DMF, DMSO, ethyl acetate, acetone, benzene, diethyl ether or mixtures thereof.

General Procedure for Making a Compound of Formula 36

To a solution of a compound of Formula 38 (about 1 eq) in acetic anhydride (about 6 eq) at 90° C. is added 1 drop of sulfuric acid (catalytic) and the resulting reaction is stirred at about 90° C. for about 2 h, and is then allowed to sit at room temperature for about 12 h. The reaction mixture is poured onto ice and the resulting solution is stirred for about 2 h, after which time the solution is neutralized to about pH 7.0 using 1 N sodium hydroxide. The resulting precipitate is filtered, washed using water (about 4×) and dried under vacuum for about 72 h to provide a compound of Formula 36.

In another embodiment, illustrated below in Scheme 9, sulfur substituted Isoquinoline Derivatives of formula 40 can be made by a method comprising contacting a compound of formula 39 and a compound of formula 11 or formula 20 in the presence of a base for a time and at a temperature sufficient to make a compound of formula 40.

Scheme 9

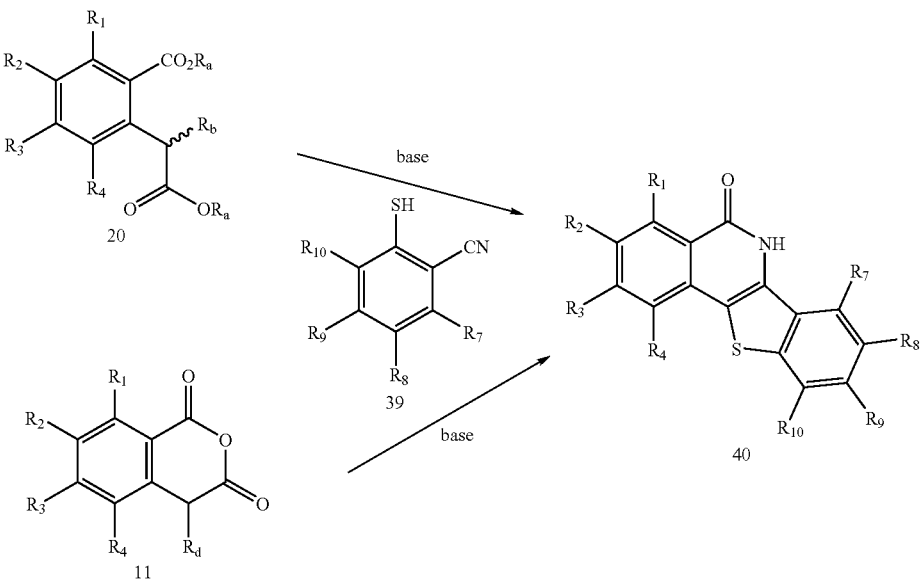

wherein

R$_1$–R$_4$ and R$_7$–R$_{10}$ are as defined above for formula (I);
each occurrence of R$_a$ is independently C$_1$–C$_3$ alkyl;
R$_b$ is —Cl, —Br, —I, —OMs, —OTs or —OTf; and
R$_d$ is —H or —Br.

In one embodiment, R$_a$ is methyl.

In another embodiment, R$_b$ is —Br.

In still another embodiment, R$_a$ is methyl and R$_b$ is —Br.

In yet another embodiment, R$_d$ is —H.

In a further embodiment, R$_d$ is —Br.

In one embodiment about 0.1 to about 10 equivalents of a compound of Formula 11a are used per about 1 equivalent of a compound of Formula 39.

In another embodiment about 0.5 to about 5 equivalents of a compound of Formula 11a are used per about 1 equivalent of a compound of Formula 39.

In still another embodiment, about 1 to about 2 equivalents of a compound of Formula 11a are used per about 1 equivalent of a compound of Formula 39.

In one embodiment about 0.1 to about 10 equivalents of a compound of Formula 11b are used per about 1 equivalent of a compound of Formula 39.

In another embodiment about 0.5 to about 5 equivalents of a compound of Formula 11b are used per about 1 equivalent of a compound of Formula 39.

In yet another embodiment, about 1 to about 2 equivalents of a compound of Formula 11b are used per about 1 equivalent of a compound of Formula 39.

In one embodiment about 0.1 to about 10 equivalents of a compound of Formula 20 are used per about 1 equivalent of a compound of Formula 39.

In another embodiment about 0.5 to about 5 equivalents of a compound of Formula 20 are used per about 1 equivalent of a compound of Formula 39.

In yet another embodiment, about 1 to about 2 equivalents of a compound of Formula 20 are used per about 1 equivalent of a compound of Formula 39.

In one embodiment about 1 to about 10 equivalents of base are used per about 1 equivalent of a compound of Formula 39.

In another embodiment about 3 to about 7 equivalents of base are used per about 1 equivalent of a compound of Formula 39.

In a yet another embodiment about 5 to about 6 equivalents of base are used per about 1 equivalent of a compound of Formula 39.

Suitable bases for use in the method of Scheme 9 are organic bases such as triethyl amine, diusopropylamine, diisopropylethylamine, pyridine, lutidine and imidazole; and inorganic bases such as alkali metal carbonates, including sodium carbonate, potassium carbonate and cesium carbonate.

In one embodiment, the base is potassium carbonate.

In another embodiment, the base is triethylamine.

The method of Scheme 9 can be carried out in the presence of a solvent, such as acetonitrile, methylene chloride, chloroform, THF, DMF, DMSO, ethyl acetate, acetone, benzene, diethyl ether, water or mixtures thereof.

In one embodiment, the solvent is DMF.

In another embodiment, the solvent is acetonitrile.

In one embodiment, the method of Scheme 9 is carried out for a time of about 1 hour to about 120 hours.

In another embodiment the method of Scheme 9 is carried out for a time of about 24 hours to about 96 hours.

In yet another embodiment the method of Scheme 9 is carried out for a time of about 60 hours to about 80 hours.

In one embodiment, the method of Scheme 9 is carried out at a temperature of about 0° C. to about 200° C.

In another embodiment, the method of Scheme 9 is carried out at a temperature of about 25° C. to about 150° C.

In still another embodiment, the method of Scheme 9 is carried out at a temperature of about 50° C. to about 100° C.

General Procedure for the Preparation Compounds of Formula 40

From a Homophthalic Anhydride:

A solution of a mercaptobenzonitrile of Formula 39 (about 1.0 eq) and a homophthalic anhydride of Formula 11 (about 2.0 eq) in a suitable solvent such as acetonitrile under inert atmosphere is warmed with stirring until all reactants are in solution. A suitable base such as triethylamine (about 1 to about 5 eq) is added and the reaction is allowed to stir at about 90° C. for about 72 hours, then cooled to room temperature. The reaction mixture is filtered, and the collected solid is washed using methanol, then dried in a vacuum oven at about 50° C. to provide a compound of Formula 40.

From a Homophthalate:

A solution of a mercaptobenzonitrile of Formula 39 (about 1.0 eq) and a homophthalate of Formula 20 (about 2.0 eq) in a suitable solvent such as acetonitrile under inert atmosphere is warmed with stirring until all reactants are in solution. A suitable base such as triethylamine (about 1 to about 5 eq) is added and the reaction is allowed to stir at about 90° C. for about 72 hours, then cooled to room temperature. The reaction mixture is filtered, and the collected solid is washed using methanol, then dried in a vacuum oven at about 50° C. to provide a compound of Formula 40.

The invention is further described in the following examples, which do not limit the scope of the invention described in the claims. The following examples illustrate the synthesis of illustrative Isoquinoline Derivatives and demonstrates their usefulness for treating or preventing an inflammatory disease or reperfusion disease.

5. EXAMPLES

Example 1

Preparation of Illustrative Isoquinoline Derivatives a) General Methods

Proton NMR spectra were obtained using a Varian 300 MHz spectrophotometer and chemical shift values (δ) are reported in parts per million (ppm). TLC was performed using TLC plates precoated with silica gel 60 F-254, and preparative TLC was performed using precoated Whatman 60A TLC plates. All intermediates and final compounds were characterized on the basis of $^1$H NMR and MS data.

b) Preparation of 5,6-dihydro-5,11-diketo-11H-indeno[1,2-c]isoquinoline (2)

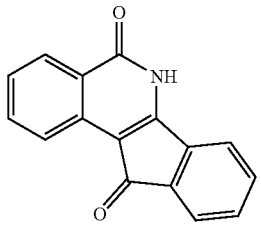

2

A stirred suspension of 1 (55 g, 0.22 mol) in NH$_3$/MeOH (7.0 N, 700 mL) was refluxed for 24 h. The reaction mixture was then allowed to cool to room temperature and was filtered and washed with MeOH to provide 46 g of the orange colored above-titled product in 84% yield. $^1$H NMR (DMSO-d$_6$): δ 7.48–7.61 (m, 4H), 7.80–7.88 (m, 1H), 7.86 (d, J=8.7 Hz, 1H), 8.22 (d, J=8.4 Hz, 1H), 8.44 (d, J=7.5 Hz, 1H), 13.05 (s, 1H); $^{13}$C NMR (DMSO-D$_6$): δ 106.33, 121.63, 122.94, 123.27, 124.80, 128.45, 132.17, 133.60, 134.03, 134.68, 134.68, 134.81, 137.09, 156.41, 163.76, 190.57; MS (ES$^{31}$): m/z 246.2 (M−1); Anal. Calcd for C$_{16}$H$_9$NO$_2$: C, 77.72; H, 3.67; N, 5.67; Found: C, 77.54; H, 3.69, N, 5.69.

c) Preparation of (±) 11-hydroxy-5,6-dihydro-5-oxo-11H-indeno[1,2-c]isoquinoline (3a)

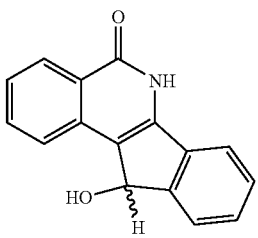

3a

To a stirred suspension of 2 (2.5 g, 0.01 mol) in EtOH (25 mL) was added NaBH$_4$ (3.75 g, 0.1 mol) at room temperature in small portions over 30 min. The reaction mixture was stirred for an additional 2 h and then cooled to 0° C. It was then triturated with 10% HCl (10% soln.). The resulting solid precipitated was filtered and washed with water and MeOH to provide 3a (2.326 g, 92%). $^1$H NMR (DMSO-d$_6$): δ 5.58 (d, J=8.1 Hz, 1H), 5.78 (d, J=8.7 Hz, 1H), 7.33–7.89 (m, 6H), 7.95 (d, J=7.8 Hz, 1H, 8.22 (d, J=7.8 Hz, 1H), 12.29 (s, 1H); $^{13}$C NMR (DMSO-d$_6$): δ 77.44, 118.81, 120.15, 124.28, 125.04, 125.67, 126.34, 128.46, 128.64, 128.95, 133.27, 135.62, 136.12, 139.93, 148.55, 163.69; MS (ES$^+$): m/z 250.1 (M+); Anal. Calcd for C$_{16}$H$_{11}$NO$_2$: C, 77.10; H, 4.45; N, 5.62. Found: C, 77.01; H, 4.57, N, 5.59.

Similarly, by reacting 2 with MeMgI and m-MeO—C$_6$H$_4$MgBr, respectively, compounds (±) 11-hydroxy-11-methyl-5,6-dihydro-5-oxo-11H-indeno[1,2-c]isoquinoline (3b) and (±) 11-hydroxy-11-(m-methoxyphenyl)-5,6-dihydro-5-oxo-11H-indeno[1,2-c]isoquinoline (3c) were prepared.

d) Preparation of 11-substituted 5,6dihydro-5-oxo-11H-indenol[1,2-c]isoquinolines (5a–e)

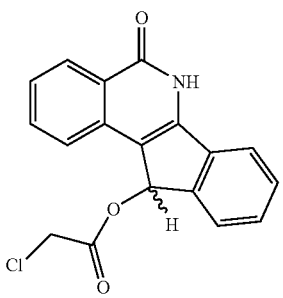

4a

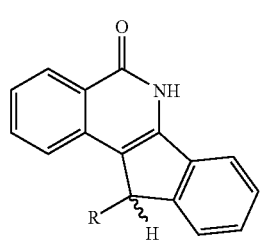

5a-e

5a: R = NMe$_2$
5b: R = NEt$_2$
5c: R = -piperidine-1-yl
5d: R = -N-methyl-piperazine-4-yl
5e: R = -morpholin-1-yl To a stirred suspension of 3a (0.5 g, 2 mmol) in pyridine (10 mL) was added chloroacetyl chloride (0.81 g, 0.006 mol) at 0° C. The reaction mixture was allowed to warm to room temperature and allowed to stir for 24 h. The reaction mixture was then poured on ice and extracted with EtOAc. The organic layer was separated, dried and concentrated to provide crude compound 4a, which was treated further with dimethylamine and stirred at room temperature for 24 h. The reaction mixture was poured on ice, and treated with 10% HCl. The resulting mixture was then basified using saturated aqueous NaHCO$_3$ and the resulting solid was filtered to provide the desired product 5a. $^1$H NMR (DMSO-D$_6$): δ 2.31 (s, 6H), 5.00 (s, 1H), 7.28–7.45 (m, 3H), 7.68–7.73 (m, 2H), 7.95 (d, J=6.9 Hz, 1H), 8.10 (d, J=7.8 Hz, 1H), 8.21 (d, J=8.1 Hz, 1H), 12.26 (s, 1H); $^{13}$C NMR (DMSO-D$_6$): δ 68.09, 116.28, 120.52, 124.58, 125.74, 126.27, 126.34, 127.68, 128.64, 133.02, 136.27, 144.45, 163.80; MS (ES$^+$): m/z 277.2 (M+1).

The following compounds were also prepared by reacting 4a as above with diethylamine, piperidine, N-methylpiperidine and morpholine, respectively:

(±) 11-diethylamino-5,6-dihydro-5-oxo-11H-indeno[1,2-c]isoquinoline (5b)

(±) 11-piperizin-5,6-dihydro-5-oxo-11H-indeno[1,2-c]isoquinoline (5c)

(±) 11-(N-methylpiperazin)-5,6-dihydro-5-oxo-11H-indeno[1,2-c]isoquinoline (5d)

(±) 11-morpholino-5,6-dihydro-5-oxo-11H-indeno[1,2-c]isoquinoline (5e).

e) Preparation of (±) 11-morpholino-5,6-dihydro-5-oxo-11H-indeno[1,2-c]isoquinolines (5e)

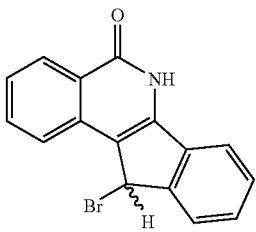

4b

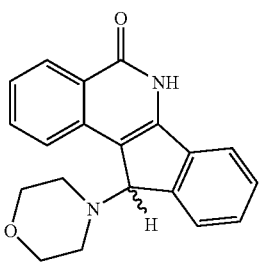

5e

To a stirred suspension of 3a (0.6 g, 2.4 mmol) in trifluoroacetic acid (5 mL) was added phosphorus tribromide (1.0 M soln. in $CH_2Cl_2$, 3 mL) at room temperature, and the reaction mixture was stirred for 8 h. The reaction mixture was poured on ice and the resulting solid was filtered to provide bromo compound 4b (0.61 g, 76%). $^1$H NMR (DMSO-$d_6$): δ 7.35–7.50 (m, 3H), 7.61 (d, J=6.6 Hz, 1H), 7.73–7.82 (m, 2H), 7.94 (d, J=6.6 Hz, 1H), 8.23 (d, J=7.8 Hz, 1H, 12.41 (s, 1H); $^{13}$C NMR (DMSO-$d_6$): δ 52.06, 79.35, 114.43 120.56, 123.58, 125.27, 125.50, 126.68, 128.55, 128.86, 129.66, 133.73, 135.91, 136.61, 141.39, 143.95, 163.74.

Compound 4b (0.5 g) was suspended in MeOH (10 mL) and treated with excess morpholine (~10 eq.) at room temperature and stirred at 60° C. for 3 h. The reaction mixture was poured on ice, and diluted with ethyl acetate (40 mL). The organic layer was separated and extracted in dil. HCl (10% soln.), the aqueous layer was then basified with sat. aq. $NaHCO_3$ and the resulting solid precipitated was filtered and dried to provide 5e (0.46 g, 90%). $^1$H NMR (DMSO-$d_6$): δ 2.56 (m, 4H), 3.49 (m, 4H), 5.04 (s, 1H), 7.31–7.45 (m, 3H), 7.65–7.76 (m, 2H), 7.96 (d, J=7.2 Hz, 1H), 8.20–8.24 (m, 2H), 12.29 (s, 1H); $^{13}$C NMR (DMSO-$D_6$): δ 49.36, 67.62, 68.11, 115.20, 120.60, 124.47, 125.84, 126.34, 126.41, 127.76, 128.30, 128.72, 133.09, 136.30, 136.96, 140.35, 144.44, 163.67.

f) Preparation of 5,6-dihydro-5-oxo-11H-indeno[1,2-c]isoquinoline (6)

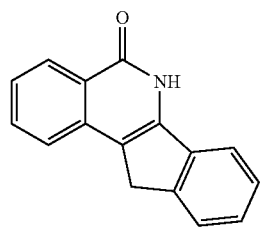

6

Method I: To a stirred solution of the alcohol 3a (0.35 g, 1.4 mmol) in trifluoroacetic acid (10 mL) was added at room temperature triethylsilane (0.812 g, 7 mmol) and the reaction mixture was stirred for 24 h. Trifluoroacetic acid was evaporated in vacuo and EtOAc was added to the resulting crude product. The resulting solid was filtered and washed with $H_2O$ and EtOAc to provide the above-titled compound 6 (0.285 g, 87%). $^1$H NMR (DMSO-$D_6$): δ 3.89 (s, 2H), 7.30–7.47 (m, 3H), 7.59 (d, J=6.9 Hz, 1H), 7.72–7.74 (m, 2H), 7.98 (d, J=7.8 Hz, 1H), 8.23 (d, J=8.4 Hz, 1H), 12.31 (s, 1H); $^{13}$C NMR(DMSO-$d_6$): 633.51, 116.50, 120.19, 124.01, 125.51, 125.55, 126.42, 127.50, 127.68, 128.56, 133.45, 136.39, 137.53, 140.18, 143.80, 163.46; MS (ES$^-$): m/z 232.1 (M−1); Anal. Calcd for $C_{16}H_{11}NO$: C, 82.38; H, 4.75; N, 6.00. Found: C, 81.79; H, 4.45, N, 5.99.

Method II: To a stirred suspension of 2 (40 g, 0.16 mol) in trifluoroacetic acid (2.5 L) was added triethylsilane (94 g, 0.8 mol) in small portions at room temperature and the reaction mixture was stirred for 96 h, during which time the reaction progress was monitored using TLC (eluent—5% MeOH/$CH_2Cl_2$). The reaction mixture was slowly poured on ice, filtered, washed with copious amounts of $H_2O$ and MeOH and dried in vacuo to provide the above-titled compound 6 (33.1 g, 88%), whose spectral data were identical to those of a sample of compound 6 that was obtained using Method I.

g) Preparation of 9-chlorosulfonyl-5,6dihydro-5-oxo-11H-indeno[1,2-c]isoquinoline (7)

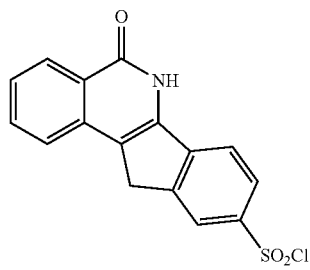

7

Compound 6 (40 g, 0.17 mol) was added in small portions to chlorosulfonic acid (112 mL, 1.71 mol) at 0° C. and the reaction mixture was allowed to warm to room temperature and allowed to stir for 2 h. The reaction mixture was slowly poured on ice and the resulting yellow solid was filtered, washed thoroughly with water and EtOAc and dried in vacuo to provide the above-titled product 7 (52 g, 92%). $^1$H NMR (DMSO-$d_6$): δ 3.91 (s, 2H), 7.43–7.48 (m, 1H), 7.60 (d, J=7.2 Hz, 1H), 7.74–7.76 (m, 2H), 7.79 (s, 1H), 7.90 (d, J=7.5 Hz, 1H), 8.23 (d, J=7.8 Hz, 1H), Anal. Calcd for $C_{16}H_{12}ClNO_4S$: C, 54.94; H, 3.46; N, 4.00. Found: C, 55.28; H, 3.43, N, 3.68, Karl-Fisher, 2.95.

h) Preparation of 9-sulphonamido derivatives of 5,6-dihydro-5-oxo-11H-indeno[1,2-c]isoquinolines (8a–af)

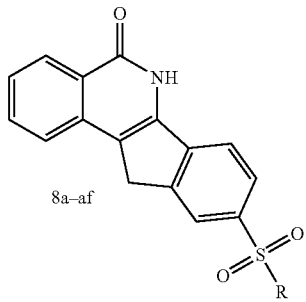

a. R = 4-Methyl-piperazine-1-yl
b. R = 4-$CH_2CO_2Me$-piperazine-1-yl
c. R = 4-$CH_2CH_2OH$-piperazine-1-yl
d. R = imidazole-1-yl
e. R = L-prolinol
f. R = morpholine-4-yl
g. R = $NHCH_2CH_2NMe_2$
h. R = $NHCH_2CH_2$-piperidine-1-yl
i. R = $NHCH_2CH_2$N-(pyridine-2-yl)
j. R = $NHCH_2CH_2$-morpholine-4-yl
k. R = $NHCH_2CH_2$-(2-N—Me-tetrahydropyrrolidine-1-yl
l. R = $NHCH_2CH_2CH_2$-morpholine-4-yl
m. R = $NHCH_2CH_2CH_2$-(tetrahydropyrrolidine-1-yl)
n. R = $NHCH_2CH_2CH_2$-imidazole-1-yl
o. R = $NHCH_2CH_2CH_2$-(4-methylpiperazine-1-yl)
p. R = $N(CH_2CH_2NEt_2)_2$
q. R = —$N(CH_2CH_2NMe_2)_2$
r. R = —$N(CH_2CH_2OH)_2$
s. R = —$NHCH_2CH_2CN$
t. R = —NHC(NH)$NH_2$
u. R = —NH[4-(1,2,4-triazole)]
v. R = —NH[4-(N-morpholine)phenyl]
w. R = —$NHCH_2CH_2$(4-N-benzylpiperidine)
x. R = —$NHCH_2CH_2$(2-thienyl)
y. R = —NH[1-(4-azabenzimidazole)]
z. R = —NH[1-(4-(2'-pyridyl)piperazine)]
aa. R = —$NHCH_2CH_2N[CH_2CH_2OH]_2$
ab. R = —NH[1-(4-benzylpiperazine)]
ac. R = —$NH_2$
ad. R = —$NHCH_2CH_2$Ph
ae. R = —$NHCH_2CH_2$[4-OMe(phenyl)]
af. R = —NHC(O)(N-morpholine)

Method I: To a stirred suspension of 3-(4-morpholino)-1-propylamine (17.28 g, 0.12 mol) in EtOAc was added sat. aq. NaHCO$_3$ (300 mL), and the mixture was allowed to stir for 15 min. Compound 7 (4.0 g, 0.012 mol) was then introduced in small portions at room temperature. The reaction mixture was stirred for 24 h; filtered and washed with H$_2$O, EtOAc and MeOH; refluxed in MeOH for 30 min; filtered while still warm; and washed with MeOH to provide compound 81 as a free base (2.33 g, 44%). $^1$H NMR (DMSO-$d_6$): δ 1.47–1.52 (m, 2H), 2.16–2.21 (m, 4H), 2.47–2.48 (m, 2H), 3.44–3.48 (m, 2H), 3.23 (m, 4H), 4.02 (s, 2H), 7.49–7.58 (m, 1H), 7.78–7.82 (m, 3H), 7.97 (s, 1H), 8.14 (d, J=7.8 Hz, 1H), 8.26 (d, J=7.8 Hz, 1H), 9.59 (s, 1H), 12.42 (s, 1H).

The free bases of 8d, 8g, 8h, 8j, 8l, 8m–8r were also prepared by Method I, but substituting 3-(4-morpholino)-1-propylamine with imidazole, 2-dimethylamino-ethylamine, 2-(N-piperidinyl)-ethylamine, 2-(N-morpholinyl)-ethylamine, 3-(N-morpholinyl)-propylamine, 3-(N-tetrahydropyrrolidinyl)-propylamine, 3-(N-imidazolyl)-propylamine, 3-(N-(4-methylpiperazinyl)-propylamine, di-(2-(diethylamino)-ethyl)amine, di-(2-(dimethylamino)-ethyl)amine and di-(2-hydroxyethyl)amine, respectively.

Method II: To a stirred suspension of 3-(4-morpholino)-1-propylamine (4.250 g) in CH$_2$Cl$_2$ (100 mL) was added 7 (1.950 g, 5.89 mmol) and the resulting mixture was stirred for 5 minutes. Subsequently, triethylamine (3 mL) was added and the reaction mixture was stirred for 24 hr at room temperature. After this time the precipitate was collected and washed with MeOH (2×10 mL) and the crude solid product transferred to a round bottom flask. This material was diluted with MeOH (200 mL), heated to reflux for 30 min. and filtered while still warm. The resulting filtercake was washed with MeOH (200 mL) to provide the desired product as the free base of 8l (1.460 g, 56%).

The free bases of compounds 8a–r were prepared using Method II, but substituting 3-(4-morpholino)-1-propylamine with about an equivalent amount of imidazole, 2-dimethylamino-ethylamine, 2-(N-piperidinyl)-ethylamine, 2-(N-morpholinyl)-ethylamine, 3-(N-morpholinyl)-propylamine, 3-(N-tetrahydropyrrolidinyl)-propylamine, 3-(N-imidazolyl)-propylamine, 3-(N-(4-methylpiperazinyl)-propylamine, di-(2-(diethylamino)-ethyl)amine, di-(2-(dimethylamino)-ethyl)amine and di-(2-hydroxyethyl)amine, respectively.

k) Preparation of the mesylate salt of 8l

Free base 8l (1.0 g) was added to methanesulfonic acid (10 mL) at 0° C. and the resulting mixture was allowed to warm to room temperature and then stirred for 2 h. The reaction mixture was then poured into cold MeOH (100 mL, between −10° C. and 0° C.) and the precipitated solid was filtered, washed with MeOH (100 mL) and dried in vacuo. The dried solid was then dissolved in water (100 mL), filtered and lyophilized to provide the methanesulfonate monohydrate salt 8l. (1.020 g, 84%). $^1$H NMR (DMSO-$d_6$): δ 1.75–1.85 (m, 2H), 2.35 (s, 3H), 2.78–2.84 (m, 2H), 2.96–3.12 (m, 4H), 3.36 (d, J=12.3 Hz, 2H), 3.61 (t, J=11.4 Hz, 2H), 3.94 (d, J=12.9 Hz, 2H), 4.03 (s, 2H), 7.49–7.55 (m, 1H), 7.76–7.84 (m, 3H), 7.99 (d, J=0.9 Hz, 1H), 8.15 (d, J=8.4 Hz, 1H), 8.25 (d, J=8.4 Hz, 1H), 9.59 (s, 1H), 12.42 (s, 1H); $^{13}$C NMR (DMSO-$d_6$): δ 24.27, 33.86, 51.89, 54.51, 64.02, 119.70, 120.39, 123.53, 126.09, 126.45, 128.63, 133.66, 135.80, 138.71, 141.21, 144.57, 163.29; Anal. Calcd for $C_{24}H_{31}N_3O_8S_2$: C, 52.06; H, 5.46; N, 7.59, Karl-Fisher, 3.36. Found: C, 51.85; H, 5.35, N, 7.30, Karl-Fisher, 4.32.

Similarly, HCl, H$_2$SO$_4$, CH$_3$COOH, and succinic acid salts of 8l were prepared by substituting methanesulfonic acid with about an equivalent amount of HCl, H$_2$SO$_4$ and CH$_3$COOH, respectively.

l) Preparation of 5,6-dihydro-5-oxo-11H-indeno[1,2-c]isoquinoline (13a)

To a solution of homophthalic anhydride (324 mg, 2.0 mmol) in acetonitrile (15 mL) was added 2-cyanobenzyl bromide (431 mg, 2.0 mmol, 1.0 eq) and triethylamine (5 mL). The reaction was stirred under inert atmosphere at room temperature for 30 minutes, after which time a yellow precipitate appeared. The reaction mixture was then heated at reflux for 18 h and the resulting white precipitate was filtered, washed using acetonitrile (3×8 mL) and dried under vacuum to provide Compound 13a as a white crystalline solid. Yield=150 mg (32%).

m) Preparation of α-Bromodimethylhomophthalate (20a)

Dimethylhomophthalate (19a) (83.1 g) was dissolved in dichloromethane (2 L) and N-bromosuccinimide (121 g, 1.7 eq) was added. The resulting suspension was irradiated for 18 h with a 500 wt quartz-halogen lamp, which brought the reaction mixture to reflux. The reaction mixture was then washed sequentially with saturated aqueous sodium bicarbonate (4 L), saturated aqueous sodium bisulfite (2 L), and saturated aqueous sodium chloride (2 L). The organic phase was dried using sodium sulfate with a small amount of silica added to remove polar impurities. The organic phase was filtered and concentrated in vacuo to provide Compound 20a as a dark orange oil. Yield=120.3 g (100%).

n) Preparation of 8-Methoxy-6H-11-oxa-6-aza-benzo[α]fluoren-5-one (22a)

α-Bromodimethylhomophthalate (20a) (1.16 g) and 2-hydroxy-5-methoxy-benzonitrile (0.6 g, 4 mmol, 1 eq) were dissolved by warming in acetonitrile (6 mL). Triethylamine (5.6 mL, 10 eq) was then added and the reaction was heated at reflux for 48 h under inert atmosphere, then cooled to room temperature. The reaction mixture was diluted with saturated sodium bicarbonate (40 mL) and the resulting suspension was allowed to stir for 2 h, and was then filtered. The filtercake was washed sequentially with 1 N HCl (2×50 mL), acetonitrile (2×50 mL) and dichloromethane (50 mL), then dried in a vacuum oven at 50° C. fot three days to provide Compound 22a as an white solid. Yield=0.81 g (76%).

o) Preparation of 8-Hydroxy-6H-11-oxa-6-aza-benzo[α]fluoren-5-one (23a)

8-Methoxy-6H-11-oxa-6-aza-benzo[a]fluoren-5-one (22a) (5.0 g) was cooled using an ice bath, and boron tribromide (1 M in methylene chloride, 95 mL, 95 mmol, 5 eq.) added in a steady stream under nitrogen. The reaction was heated at reflux under inert atmosphere for two hours, then cooled to room temperature and poured into water (150 mL). The resulting suspension was allowed to stir for 1 h, filtered, and the solids were washed with water (2×200 mL). The solids were then diluted with 5 N sodium hydroxide (600 mL) using heating. The resulting solution was cooled to 0° C. using an ice bath and the solution was acidified to pH 1 using conc. HCl. The resulting precipitate was vacuum filtered, and the solids washed sequentially with water (3×300 mL) and diethyl ether (300 mL) then dried overnight using a vacuum oven at 50° C. to provide Compound 23a as a gray solid. Yield=4.74 g (100%).

p) Preparation of 3-Nitroso-2-Phenyindole (28)

A solution of 2-phenylindole (27) (25 gm, 0.129 mol) in acetic acid (250 mL) was cooled to 18° C. and a solution of sodium nitrite (8 g, 0.115 mol) in water (10 mL) was added dropwise while keeping the temperature of the reaction at ca. 20° C. The resulting reaction was stirred for 30 min at room temperature then diluted with ice water (250 mL). The reaction mixture was was filtered and the solid was washed with water then recrystallized using methanol to provide Compound 28. Yield=27.5 gm (96.4%). ES-MS: 223.22 (M$^+$+1); NMR (DMSO-d$_6$): 7.0 (m, 1H), 7.1 (m, 1H), 7.22 (m, 1H), 7.32 (m, 2H), 7.40 (m, 1H), 7.48 (m, 2H), 7.60 (m, 1H).

q) Preparation of 3-Amino-2-Phenylindole (29)

To a solution of 3-nitroso-2-phenyl indole (28) (25 gm, 0.129 mol) in ethanol (450 ml) was added 2N sodium hydroxide (300 mL, 5.0 eq) followed by sodium dithionite (38 g). The reaction was heated at reflux for 5 h, then filtered. The solid was washed with water and dried under vacuum to provide Compound 29 as a yellow solid. Yield=15 g (72.1%). ES-MS: 209.25 (M$^+$+1); NMR (DMSO-d$_6$): 7.0 (m, 1H), 7.1 (m, 1H), 7.22 (m, 1H), 7.32 (m, 2H), 7.40 (m, 1H), 7.48 (m, 2H), 7.60 (m, 1H).

r) Preparation of 2-Phenylindole-3-ethylcarbamate (30)

To a 0° C. solution of 3-amino-2-phenylindole (29) (1.7 g, 8.17 mmol) in dichloromethane (150 ml) was added triethylamine (5 mL, 4.5 eq) followed by ethyl chloroformate (1 mL). The reaction was allowed to stir for 15 hours, after which time the reaction mixture was diluted with water and transferred to a separatory funnel. The dichloromethane (50 mL), washed with water (2×50 mL), brine (50 mL) and dried over sodium sulfate. The solvent was removed and dried under vacuum to provide Compound 30 as a black solid (1.6 gm, 72.7%). ES-MS: 281.25 (M$^+$+1); NMR (DMSO-d$_6$): 1.30 (t,3H), 4.12 (t, 2H), 7.0 (m, 1H), 7.1 (m, 1H), 7.22 (m,2H), 7.32 (m, 2H), 7.40 (m, 1H), 7.48 (m, 2H), 7.60 (m, 1H).

s) Preparation of 6H,11H-Indole-[3,2–C]-Isoquinoline-5-one (31)

A solution of 2-Phenylindole-3-aminoethylcarbamate (30) (1.4 g, 5 mmol) in diphenyl ether (10 ml) was heated at reflux for 4 h, then cooled to room temperature. The reaction mixture was filtered and the solid was washed sequentially using warm hexane and warm dichloromethane and dried under vacuum to provide Compound 31 as a gray solid. Yield=1.6 g (72.7%). ES-MS: 235.25 (M$^+$+1); NMR (DMSO-d$_6$): 7.1 (t, 1H), 7.25 (t, 1H), 7.50 (m, 2H), 7.82 (t, 1H), 8.0 (d, 1H), 8.14 (d, 1H), 8.32 (t, 1H), 11.7 (s, 1H), 12.2 (s, 1H).

t) Preparation of 6H,11H-Indole-[3,2–C]-Isoquinoline-5-one-5,11-diacetate (32)

To a 0° C. solution of 6H,11H-Indole-[3,2-C]-Isoquinoline-5-one (31) (117 mg, 0.5 mmol) in dichloromethane (10 mL) was added triethylamine (2 mL, 30 eq) followed by acetic anhydride (1.8 mL, 35 eq). The reaction was stirred at room temperature for 48 hrs, then poured over ice and extracted with dichloromethane (100 mL). The dichloromethane layer was washed sequentially using water (2×20 mL) and brine (25 mL), then dried using sodium sulfate and concentrated in vacuo. The resulting solid residue was dried under vacuum to provide Compound 32 as a brown solid. Yield=180 mg, 83.7%. ES-MS: 430.57 (M$^+$+1).

u) Preparation of 6H,11H-Indole-[3,2–C]-Isoquinoline-5-one-9,11-disulfonylchloride (33)

Compound 31 (117 mg, 0.5 mmol) was added to chlorosulfonic acid (2 mL, 60 eq) and the resulting reaction mixture was allowed to stir at room temperature for 4 hours, after which time the reaction mixture was poured over ice. The resulting precipitate was filtered, washed sequentially with water and ethyl acetate and dried under vacuum to provide Compound 33 as a light-yellow solid. Yield=180 mg (83.7%). ES-MS: 430.57 ($M^++1$); NMR (DMSO-$d_6$): 7.1 (t, 1H), 7.25 (t, 1H), 7.50 (m, 2H), 7.82 (t, 1H), 8.0 (d, 1H), 8.14(d, 1H), 8.32 (t, 1H), 11.7 (s, 1H), 12.2 (s, 1H).

v) Preparation of 6H,11H-Indole-[3,2–C]-Isoquinoline-5-one -9,11-disulfonamide (35a).

To a solution of 33 (215 mg, 0.5 mmol) in methanol (10 mL) at 0° C. was added a 20% solution of ammonia in methanol (10 mL). The reaction mixture was allowed to stir at room temperature for 15 hours and was then filtered. The resulting solid was washed with methanol and the dried under vacuum to provide Compound 35a as a yellow solid. Yield=140 mg *71.4%). ES-MS: 392.81 ($M^++1$).

w) Preparation of N-acetylanthranilonitrile (36a)

To a solution of anthranilonitrile (4.0 g, 32 mmol) in acetic anhydride (18 mL, 5.5 eq) at 90° C. was added 1 drop of sulfuric acid and the resulting reaction was stirred at 90° C. for 2 h, then allowed to sit at room temperature for 12 h. The reaction mixture was poured onto ice (ca. 200 mL) and the resulting solution was stirred for 2 h, after which time the solution was neutralized to pH 7.0 using 5 N sodium hydroxide. The resulting precipitate was filtered, washed using water (4×50 mL) and dried under vacuum for 72 h to provide Compound 36a as a white crystalline solid. Yield=1.07 g (16%).

x) Preparation of 6H,11H-indolo[3,2-c]isoquinolin-5-one (37a)

From α-Bromodimethylhomophthalate:

α-Bromodimethylhomophthalate (20a) (603 mg, 2.1 mmol) and N-acetylanthranilonitrile (36a) (370 mg, 1.1 eq) were dissolved in DMF (5 mL) under inert atmosphere. Potassium carbonate (1.45 g, 5.0 eq) was added and the reaction was stirred for 48 h at 100° C., then cooled to room temperature. The reaction mixture was poured into 1 N sodium hydroxide and the resulting mixture was extracted with EtOAc (50 mL). The EtOAc layer was washed sequentially with 1N HCl (50 mL), saturated aqueous sodium chloride (50 mL), dried over sodium sulfate, filtered and concentrated in vacuo. The resulting residue was dissolved by warming in toluene (70 mL) and the solution was cooled to room temperature and upon addition of hexanes (200 mL), a solid precipitate appeared. The solid precipitate was filtered, washed using hexanes (50 mL) and dried in a vacuum oven at 50° C. for 72 h to provide Compound 37a as a yellow powder. Yield=33 mg (6.7%).

y) Preparation of 6H,11H-thia-6-aza-benzol[a]fluorene-5-one (40a)

From homophthalic anhydride:

A solution of 2-mercaptobenzonitrile (39a) (1.35 g, 10 mmol) and homophthalic anhydride (11a) (1.6 g, 10.0 mmol, 1.0 eq) in acetonitrile (150 mL) under inert atmosphere was warmed with stirring until all reactants were in solution. Triethylamine (6.9 mL, 50 mmol, 5.0 eq) was added and the reaction was heated at reflux for 72 hours, then cooled to room temperature. After cooling, the reaction mixture was filtered, and the collected solid was washed using methanol (3×50 mL), then dried in a vacuum oven at 50° C. to provide Compound 40a as a white solid. Yield=225 mg (9%).

From α-bromodimethylhomophthalate:

A solution of 2-mercaptobenzonitrile (39a) (1.35 g, 10 mmol) and α-bromodimethylhomophthalate (20a) (2.87 g, 10.0 mmol, 1.0 eq) in acetonitrile (150 mL) under inert atmosphere was warmed with stirring until all reactants were in solution. Triethylamine (6.9 mL, 50 mmol, 5.0 eq) was added and the reaction was heated at reflux for 72 hours, then cooled to room temperature. After cooling, the reaction mixture was filtered, and the collected solid was washed using methanol (3×50 mL), then dried in a vacuum oven at 50° C. to provide Compound 40a as a white solid. Yield=250 mg (10%).

Example 2

Effect of Illustrative Isoquinoline Derivatives on PARS activity in cultured macrophages, using a whole-cell based assay and a purified enzyme assay.

Demonstration of illustrative Isoquinoline Derivatives' ability to inhibit PARS and prevent peroxynitrite induced cytotoxicity was shown using methods described in Virag et al., *Br J Pharmacol*. 1999, 126(3):769–77; and *Immunology* 1998, 94(3):345–55. RAW mouse macrophages were cultured in DMEM medium with high glucose and supplemented with 10% fetal bovine serum. Cells were used at 80% confluence in 12-well plates. Cells were pretreated with various concentrations (100 nM–1 μM) of an Isoquinoline Derivative for 10 min. Peroxynitrite, a prototypical oxidant which induces DNA single strand breakage, was used to induce PARS activation. Peroxynitrite was diluted in phosphate buffered saline (PBS) (pH 11.0) and added to the cells in a bolus of 50 μl. Cells were then incubated for 20 min. Peroxynitrite was decomposed by incubation for 30 min at pH 7.0, used as a control, and failed to influence the parameter studied. After the 20 min incubation, the cells were spun, the medium was aspirated and the cells were resuspended in 0.5 ml assay buffer (56 mM HEPES pH 7.5, 28 mM KCl, 28 mM NaCl, 2 mM $MgCl_2$, 0.01% w/v digitonin and 0.125 μM $NAD^+$ and 0.5 μCi/ml$^3$H-$NAD^+$). Following an incubation in assay buffer, (10 min at 37° C.), PARS activity was measured as follows: 200 μl ice cold 50% w/v TCA was added and the samples were incubated for 4 hours at 4° C. Samples were then spun (10 min @ 10,000 g) and pellets washed twice with ice cold 5% w/v TCA and solubilized overnight in 250 μl 2% w/v SDS/0.1 N NaOH at 37° C. The contents of the tubes were added to 6.5 ml ScintiSafe Plus scintillation liquid (Fisher Scientific) and radioactivity was determined using a liquid scintillation counter (Wallac, Gaithersburg, Md.). The results shown in Table 1 demonstrate that the illustrative Isoquinoline Derivatives significantly and dose-dependently inhibit the activation of PARS in the macrophage assay.

TABLE 1

Inhibitory effect of various novel substituted isoquinolines on PARS activation in cultured murine macrophages.

| Compound No. | % PARS inhibition at 1 µM | % PARS inhibition at 300 nM | % PARS inhibition at 100 nM |
|---|---|---|---|
| 2 | 60 | NT | 16 |
| 3a | 67 | NT | 8 |
| 3b | 25 | 0 | NT |
| 3c | 21 | 9 | NT |
| 4b | 88 | NT | 51 |
| 5a | 55 | NT | 10 |
| 5b | 33 | NT | 0 |
| 5c | 24 | NT | 0 |
| 5d | 48 | NT | 0 |
| 5e | 21 | NT | 0 |
| 6 | 65 | NT | 30 |
| 7 | 50 | NT | 0 |
| 8a | NT | 47 | NT |
| 8c | NT | 27 | NT |
| 8d | NT | 82 | 77 |
| 8e | NT | 68 | NT |
| 8g | NT | 55 | 34 |
| 8h | NT | 76 | 56 |
| 8j | NT | 76 | 34 |
| 8k | NT | 38 | 24 |
| 8l | NT | 84 | 34 |
| 8m | NT | 50 | NT |
| 8n | NT | 82 | 74 |
| 8o | NT | 55 | 48 |
| 8p | NT | 45 | 27 |
| 8q | NT | 28 | 20 |
| 8r | NT | 28 | 20 |
| 8s | 54 | NT | 30 |
| 8t | 29 | NT | 17 |
| 8u | NT | NT | 59 |
| 8w | NT | NT | 69 |
| 8x | NT | NT | 54 |
| 8y | NT | NT | 59 |
| 8z | NT | NT | 67 |
| 8aa | NT | NT | 64 |
| 8ab | NT | NT | 49 |
| 8ag | 59 | NT | 35 |
| 8ah | 63 | NT | 67 |
| 8ai | 90 | NT | 69 |
| 8ak | NT | 22* | 8* |
| 8al | 84 | NT | 49 |
| 8am | NT | NT | 65* |
| 8an | 40* | NT | 40* |
| 8ao | 60 | NT | 40 |
| 10a | NT | 59 | 55 |
| 10b | NT | 17 | 17 |
| 22a | 81 | NT | 51 |
| 22b | NT | 20* | 12* |
| 22c | 83 | 66 | 62 |
| 22d | 13* | NT | NT |
| 22e | 53 | 56 | 38 |
| 22f | 27 | 23 | NT |
| 22g | 27 | 23 | NT |
| 23a | 84 | 79 | 34 |
| 23b | 58 | 57 | 53 |
| 23c | 63 | 66 | 63 |
| 25a | 51 | 57 | 53 |
| 25b | 40 | 29 | 25 |
| 25c | 58 | 34 | 23 |
| 25d | 67 | 66 | 53 |
| 25e | 58 | 63 | 40 |
| 26a | 90 | 74 | 51 |
| 26b | 51* | 29* | 21* |
| 31 | 67 | 57 | 18 |
| 34 | NT | 33* | 14* |
| 35a | 75 | 55 | 14 |
| 35b | 42 | 51 | 25 |

NT—Not Tested
*tested in purified enzyme assay

The potency of inhibition on purified PARS enzyme was subsequently determined for selected Isoquinoline Derivatives, and the potency was compared with that of 3-aminobenzamide, a prototypical benchmark PARS inhibitor. The assay was performed in 96 well ELISA plates according to instructions provided with a commercially available PARS inhibition assay kit (Trevigen, Gaithersburg, Md.). Briefly, wells were coated with 1 mg/mL histone (50 µl/well) at 4° C. overnight. Plates were then washed four times with PBS and then blocked by adding 50 µl Strep-Diluent (supplied with the kit). After incubation (1 h, room temperature), the plates were washed four times with PBS. Appropriate dilutions of PARS inhibitors were combined with 2×PARS cocktail (1.95 mM $NAD^+$, 50 µM biotinylated $NAD^+$ in 50 mM TRIS pH 8.0, 25 mM $MgCl_2$) and high specific activity PARS enzyme (both were supplied with the kit) in a volume of 50 µl. The reaction was allowed to proceed for 30 min at room temperature. After 4 washes in PBS, incorporated biotin was detected by peroxidase-conjugated streptavidin (1:500 dilution) and TACS Sapphire substrate. The assay confirmed the results of the macrophage-based PARS assay. For example, the PARS inhibitor 8l exerted 50% inhibition of PARS activity in this assay at 3 nM, and thus was approximately 50,000 times more potent than the reference compound 3-aminobenzamide.

Example 3

Effects of illustrative Isoquinoline Derivatives in Various Models of Inflammatory Disease and Reperfusion Disease a: Effects of illustrative Isoquinoline Derivatives on in vitro Cell Disease Models In additional in vitro studies in isolated thymocytes, cells were exposed to peroxynitrite or hydrogen peroxide (toxic oxidant species) to induce cytotoxicity. In this system the toxicity is, at least in part, related to activation of the nuclear enzyme PARS. In this oxidant-stimulated thymocyte assay (described, in detail, in Virag et al., *Immunology* 94(3): 345–55, 1998), the compounds tested prevented the oxidant-induced suppression of the viability of the cells and did so at the low nanomolar concentration range. An example of this response (Compound 8l) is shown in Table 2. This assay represents an in vitro model of cells dying because of exposure to pro-oxidant species, as it occurs in during the reperfusion of ischemic organs.

TABLE 2

Reduction of peroxynitrite induced cytotoxicity by 30 nM–3 µM of the Isoquinoline Derivative 8l.

| | Control | +8l 30 nM | +8l 100 nM | +8l 300 nM | +8l 1 µM | +8l 3 µM |
|---|---|---|---|---|---|---|
| Cytotoxicity | 98% | 74% | 39% | 2% | 0% | 0% | b: Effect of illustrative Isoquinoline Derivatives on in vivo Models of Inflammatory Diseases In order to substantiate the efficacy of the compounds in inflammatory diseases, the effect of illustrative Isoquinoline Derivatives was demonstrated in a systemic inflammatory model induced by bacterial lipopolysaccharide (LPS), which is reported to be responsible for causing reperfusion diseases and inflammatory diseases such as septic shock and systemic inflammatory response syndrome in animals (see Parrillo, *N. Engl. J. Med.*, 328:1471–1478 (1993) and Lamping, *J. Clin. Invest.* 101:2065–2071 (1998). In a series of experiments, mice were pretreated with intraperitoneal injection of 0.1 and 1 mg/kg of compounds 81, 8p and 8j, and LPS at 10 mg/kg was injected i.p., and TNF-alpha was measured in the plasma at 90 minutes. As shown in Table 3, all compounds substantially reduced TNF production, indicative of the compounds' anti-inflammatory activity.

TABLE 3

Reduction of LPS induced TNF production by 0.1–1 mg/kg intraperitoneal injection of the PARS inhibitor compounds 8L, 8P and 8J in mice in vivo

|  | 8j (0.1 mg/kg) | 8j (1.0 mg/kg) | 8p (0.1 mg/kg) | 8p (1.0 mg/kg) | 8l (0.1 mg/kg) | 8l (1.0 mg/kg) | Vehicle |
|---|---|---|---|---|---|---|---|
| TNF (ng/ml) | 3831.6 ± 385.2 | 5038.8 ± 377.1 | 4470.0 ± 184.4 | 5090.8 ± 203.7 | 3714.6 ± 300.9 | 3509.8 ± 311.5 | 6994.0 ± 904.4 |

All compounds markedly suppressed LPS induced TNF production when compared to control.

At high doses, LPS causes multiple organ dysfunction resembling of septic shock, and ultimately death (in part because of the early release of TNF-alpha). Similarly, in a model induced by cecal ligation and puncture (CLP), the live bacteria that derive from the intestinal flora induce systemic inflammation and shock. Agents that inhibit inflammatory mediator production, PARS activation, and cell death in this model prevent mortality induced by LPS or CLP. In experiments with Balb/c mice, injection of 100 mg/kg LPS intraperitoneally caused death in 50% of the animals over 24 h, whereas treatment of the animals with 3 mg/kg/day of compound 81 reduced the endotoxin-induced mortality to 10% under the same experimental conditions. In response to CLP induced shock, compound 81 (3 mg/kg/day) caused a reduction in the mortality from 100% death to 60% death over 24 hours.

The data demonstrating the reduction of TNF production by illustrative Isoquinoline Derivatives in animals subjected to an inflammation model, coupled with the fact that TNF production is an important trigger of inflammation in various inflammatory diseases (such as, for example, colitis, arthritis and neuroinflammation and shock) indicate that the Isoquinoline Derivatives have therapeutic effects in various systemic and local inflammatory diseases, including the rejection of transplanted organs, which entails both an inflammatory disease component and a reperfusion disease component and, accordingly, are useful for treating or preventing an inflammatory disease or a reperfusion disease.

c: Effect of illustrative Isoquinoline Derivatives on in vivo Models of Reperfusion Disease In order to substantiate the efficacy of the Isoquinoline Derivatives in ischemia-reperfusion conditions, the effect of an illustrative Isoquinoline Derivative in a mouse model of ischemic and reperfused gut was tested. The superior mesenteric artery was occluded for 45 min, followed by a reperfusion for 1 h. Following the end of the reperfusion, gut permeability was measured with the FD4 method in evened gut sacks (Liaudet et al; *Shock* 2000, 14(2):134–41). Ischemia-reperfusion increased the permeability of the gut from 11±4 to 216±27 ml/min/cm$^2$, indicative of severe damage of the reperfused gut. Treatment with Compound 81 (3 mg/kg i.v., injected 10 min. prior to initiation of reperfusion) reduced the increase in the permeability of the gut by approximately 73%, indicating a marked maintenance of the gut function. The ischemia-reperfusion studies in the gut were associated with a 80% mortality over 12 hours, whereas only 15% mortality was noted in the animals treated with 81.

In another set of experiments, the effect of Compound 81 in a rat model of middle cerebral artery occlusion/reperfusion was assayed as described in Abdelkarim et al., *Int J Mol Med.* 2001, 7(3):255–60. Occlusion lasted for 2 hours, followed by reperfusion for 24 hours. Infarct size was quantified with tetrazolium staining. Compound 81 was administered at 3 mg/kg/day in 3 divided intraperitoneally injected doses, the first dose being administered 10 min. prior to the initiation of reperfusion. There was an approximately 80% reduction in the degree of cortical necrosis and neuronal death in the animals administered with 81, when compared to vehicle-treated controls. This protection also translated into functional benefit, such as neurological improvements in the PARS inhibitor treated group.

These data indicate that the Isoquinoline Derivatives have therapeutic effects in various systemic and local conditions of reperfision diseases, including the rejection of transplanted organs, which entails both an inflammatory disease component and a reperfusion disease component and, accordingly, are useful for treating or preventing an inflammatory disease or a reperfusion disease.

d: Effect of illustrative Isoquinoline Derivatives in a Diabetes Model

PARS inhibitors and PARS deficiency are known to reduce the development of diabetes and the incidence of diabetic complications (Mabley et al., *Br J Pharmacol.* 2001, 133(6):909–9; and Soriano et al., *Nat Med.* 2001, 7(1):108–13). In order to substantiate the efficacy of the Isoquinoline Derivatives in a diabetes model, a single high-dose streptozotocin model of diabetes was conducted as previously described. Briefly, 160 mg/kg streptozotocin was injected to mice treated with vehicle or with illustrative Isoquinoline Derivatives intraperitoneally (3 mg/kg) and 3 days later blood sugar levels were determined using a blood glucose meter. The data shown in Table 4 demonstrate that the illustrative Isoquinoline Derivatives attenuate the streptozotocin-induced onset of diabetes as they reduce the hyperglycemia.

TABLE 4

Reduction of streptozotocin (STZ) induced hyperglycemia by 3 mg/kg intraperitoneal injection of the PARS inhibitor compounds 8l, 8p and 8j in mice in vivo

|  | Basal | STZ + Vehicle | STZ + 8j | STZ + 8p | 8l |
|---|---|---|---|---|---|
| Glucose (mg/ml) | 153 ± 21 | 320 ± 13 | 253 ± 24 | 264 ± 24 | 244 ± 21 |

Accordingly, the Isoquinoline Derivatives are useful for treating or preventing diabetes or a diabetic complication.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited, the entire disclosures of which have been incorporated herein in their entirety.

What is claimed is:

1. A process for preparing a compound of formula 37

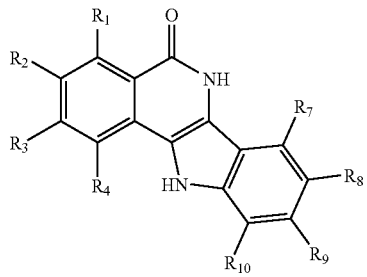

wherein:
$R_1$, $R_2$, $R_3$, $R_4$, $R_7$, $R_8$, $R_9$ and $R_{10}$ are independently -hydrogen, -halo, -hydroxy, -O-($C_1$-$C_5$alkyl), $C_1$-$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), $NO_2$ or —A—B;

A is —$SO_2$—, —$SO_2$NH—, —NHCO—, —NHCONH—, —O—, —CO—, —OC(O)—, —C(O)O—, —CONH—, —CON($C_1$-$C_4$ alkyl)-, —NH—, —$CH_2$—, —S— or —C(S)—;

B is —$C_1$-$C_{10}$ alkyl, —$C_2$-$C_{10}$ alkenyl, -heterocycle, —$C_3$-$C_8$ carbocycle, -aryl, —$NZ_1Z_2$, —($C_1$-$C_5$ alkylene)-$NZ_1Z_2$, -alkylamino, -aminodialkyl, -alkylheterocycle, -arylamido, —C(O)OH, —C(O)O—($C_1$-$C_5$ alkyl), —C(O)O-phenyl or —C(NH)$NH_2$ any of which are unsubstituted or substituted with one or more of —O—($C_1$-$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$-$C_{10}$ alkyl, —$C_2$-$C_{10}$ alkenyl, —$C_2$-$C_{10}$ alkynyl, -aryl, -benzyl, -alkylamido, -alkylcarboxy, —C(O)OH, —$C_1$-$C_5$ alkylene-C(O)O—($C_1$-$C_5$ alkyl) or —$C_1$-$C_5$ alkylene-OC(O) ($C_1$-$C_5$ alkyl); and $Z_1$ and $Z_2$ are independently —H or —$C_1$-$C_{10}$ alkyl, which is unsubstituted or substituted with one or more of -halo, —OH or —N($Z_3$)($Z_4$), where $Z_3$ and $Z_4$ are independently, —H or —$C_1$-$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine, comprising contacting a compound of formula 36

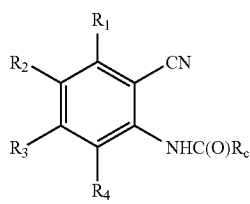

wherein
$R_c$ is $C_1$-$C_3$ alkyl, with a compound of formula 11a or a compound of formula 20

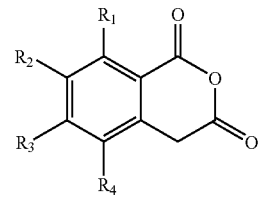

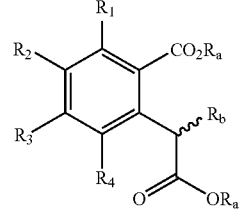

wherein
each occurrence of $R_a$ is independently $C_1$-$C_3$ alkyl; and $R_b$ is —Cl, —Br, —I, —OMs, —OTs or —OTf, in the presence of a base, for a time and at a temperature sufficient to make the compound of formula 37.

2. A method for treating Parkinson's disease, the method comprising administering to a subject in need thereof an effective amount of a compound or a pharmaceutically acceptable hydrate or salt of a compound having the formula:

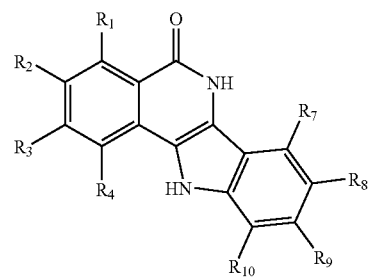

wherein:
$R_1$, $R_2$, $R_3$, $R_4$, $R_7$, $R_8$, $R_9$ and $R_{10}$ are independently -hydrogen, -halo, -hydroxy, —O—($C_1$-$C_5$ alkyl), —$C_1$-$C_{10}$ alkyl, -alkylhalo, —$C_2$-$C_{10}$ alkenyl, —$C_3$-$C_8$ carbocycle, -aryl, —$NH_2$, -alkylamino, —C(O)OH, —C(O)O($C_1$-$C_5$ alkyl), —OC(O)($C_1$-$C_5$ alkyl), —$NO_2$ or —A—B;

A is —$SO_2$—, —$SO_2$NH—, —NHCO—, —NHCONH—, —O—, —CO—, —OC(O)—, —C(O)O—, —CONH—, —CON($C_1$-$C_4$ alkyl)—, —NH—, —$CH_2$—, —S— or —C(S)—;

B is —$C_1$-$C_{10}$ alkyl, —$C_2$-$C_{10}$ alkenyl, -heterocycle, —$C_3$-$C_8$ carbocycle, -aryl, —$NZ_1Z_2$, —($C_1$-$C_5$ alkylene)-$NZ_1Z_2$, -alkylamino, -aminodialkyl, -alkylheterocycle, -arylamido, —C(O)OH, —C(O)O—($C_1$-$C_5$ alkyl), —C(O)O-phenyl or —C(NH)$NH_2$, any of which are unsubstituted or substituted with one or more of —O—($C_1$-$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -arylamido, -alkylcarboxy, —C(O)OH, —$C_1$–$C_5$ alkylene-C(O)O—$C_1$–$C_5$ alkyl or —$C_1$–$C_5$ alkylene-OC(O)—$C_1$–$C_5$ alkyl groups; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine.

3. A pharmaceutical composition comprising an effective amount of a compound or pharmaceutically acceptable salt or hydrate of a compound having the formula:

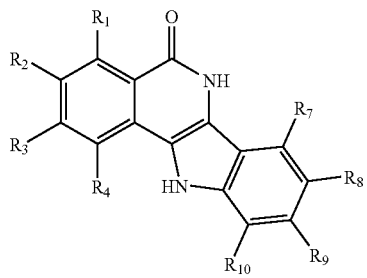

wherein:

$R_1$, $R_2$, $R_3$, $R_4$, $R_7$, $R_8$, $R_9$ and $R_{10}$ are independently -hydrogen, -halo, -hydroxy, —O—($C_1$–$C_5$ alkyl), —$C_1$–$C_{10}$ alkyl, -alkylhalo, —$C_2$–$C_{10}$ alkenyl, —$C_3$–$C_8$ carbocycle, -aryl, —$NH_2$, -alkylamino, —C(O)OH, —C(O)O($C_1$–$C_5$ alkyl), —OC(O)($C_1$–$C_5$ alkyl), —$NO_2$ or —A—B;

A is —$SO_2$—, —$SO_2NH$—, —NHCO—, —NH-CONH—, —O—, —CO—, —OC(O)—, —C(O)O—, —CONH—, —CON($C_1$–$C_4$ alkyl)—, —NH—, —$CH_2$—, —S— or —C(S)—;

B is —$C_1$–$C_{10}$ alkyl, —$C_2$–$C_{10}$ alkenyl, -heterocycle, —$C_3$–$C_8$ carbocycle, -aryl, —$NZ_1Z_2$, —($C_1$–$C_5$ alkylene)-$NZ_1Z_2$, -alkylamino, -aminodialkyl, -alkylheterocycle, -arylamido, —C(O)OH, —C(O)O—($C_1$–$C_5$ alkyl), —C(O)O-phenyl or —C(NH)$NH_2$, any of which are unsubstituted or substituted with one or more of —O—($C_1$–$C_5$ alkyl), -halo, -alkylhalo, -alkanol, -alkylamino, -hydroxy, —$NO_2$, —$NH_2$, —CN, -aminoalkyl, -aminodialkyl, -heterocyclic amine, —$C_1$–$C_{10}$ alkyl, —$C_2$–$C_{10}$ alkenyl, —$C_2$–$C_{10}$ alkynyl, -aryl, -benzyl, -arylamido, -alkylcarboxy, —C(O)OH, —$C_1$–$C_5$ alkylene-C(O)O—$C_1$–$C_5$ alkyl or —$C_1$–$C_5$ alkylene-OC(O)—$C_1$–$C_5$ alkyl groups; and $Z_1$ and $Z_2$ are independently —H or —$C_1$–$C_{10}$ alkyl, which is unsubstituted or substituted with one or more of -halo, —OH or —N($Z_3$)($Z_4$), where $Z_3$ and $Z_4$ are independently, —H or —$C_1$–$C_5$ alkyl, which is unsubstituted or substituted with one or more of -halo, -hydroxy or —$NH_2$; or N, $Z_3$ and $Z_4$ are taken together to form an unsubstituted or substituted heterocyclic amine; or N, $Z_1$ and $Z_2$ are taken together to form a heterocyclic amine, and a pharmaceutically acceptable carrier.

4. A compound having the formula:

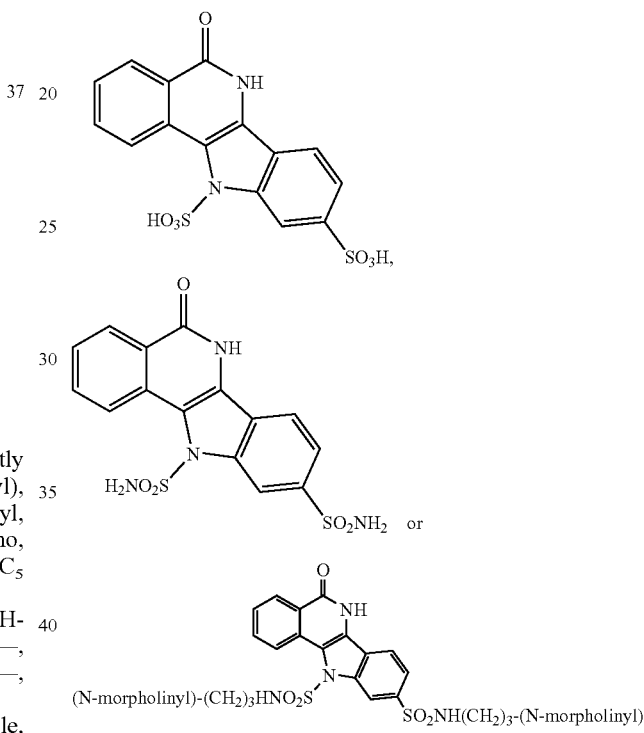

or a pharmaceutically acceptable salt thereof.

5. A method for treating Parkinson's disease, the method comprising administering to a subject in need thereof an effective amount of the compound or a pharmaceutically acceptable salt of the compound of claim 4.

* * * * *